(12) United States Patent
Abe et al.

(10) Patent No.: US 9,630,971 B2
(45) Date of Patent: Apr. 25, 2017

(54) FREE BASE CRYSTALS

(71) Applicants: TAKEDA PHARMACEUTICAL COMPANY LIMITED, Osaka-shi, Osaka (JP); INTRA-CELLULAR THERAPIES, INC., New York, NY (US)

(72) Inventors: Takashi Abe, Osaka (JP); Graham Buckton, Hampshire (GB); Robert Davis, San Diego, CA (US); Mark Hooper, Oxfordshire (GB); Peng Li, New Milford, NJ (US); Hideaki Maruyama, Osaka (JP); Masahiro Takasuga, Osaka (JP); Lawrence P. Wennogle, Hillsborough, NJ (US); Yuhei Yamamoto, Osaka (JP); Hironori Yamashita, Osaka (JP)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 14/900,589

(22) PCT Filed: Jun. 20, 2014

(86) PCT No.: PCT/US2014/043422
§ 371 (c)(1),
(2) Date: Dec. 21, 2015

(87) PCT Pub. No.: WO2014/205354
PCT Pub. Date: Dec. 24, 2014

(65) Prior Publication Data
US 2016/0145261 A1    May 26, 2016

Related U.S. Application Data

(60) Provisional application No. 61/838,105, filed on Jun. 21, 2013, provisional application No. 61/919,424, filed on Dec. 20, 2013.

(51) Int. Cl.
*A61K 31/519*    (2006.01)
*C07D 487/14*    (2006.01)

(52) U.S. Cl.
CPC .................................. *C07D 487/14* (2013.01)

(58) Field of Classification Search
CPC ...................................................... A61K 31/519
See application file for complete search history.

(56) References Cited

U.S. PATENT DOCUMENTS

| | | |
|---|---|---|
| 8,273,750 B2 | 9/2012 | Li et al. |
| 8,273,751 B2 | 9/2012 | Li |
| 8,536,159 B2 | 9/2013 | Li et al. |
| 8,633,180 B2 | 1/2014 | Li et al. |
| 8,664,207 B2 | 3/2014 | Li et al. |
| 8,829,008 B2 | 9/2014 | Li |
| 8,858,911 B2 | 10/2014 | Li et al. |
| 9,000,001 B2 | 4/2015 | Li et al. |
| 9,006,258 B2 | 4/2015 | Fienberg et al. |
| 9,198,924 B2 | 12/2015 | Mates et al. |
| 2001/0034450 A1 | 10/2001 | Alexander et al. |
| 2004/0152712 A1 | 8/2004 | Bunnage et al. |
| 2005/0075795 A1 | 4/2005 | Pandit |
| 2005/0080107 A1 | 4/2005 | Ochiai et al. |
| 2008/0188492 A1 | 8/2008 | Li et al. |
| 2010/0087450 A1 | 4/2010 | Mates et al. |
| 2010/0273754 A1 | 10/2010 | Li et al. |
| 2010/0323997 A1 | 12/2010 | Fienberg |
| 2011/0237561 A1 | 9/2011 | Li et al. |
| 2011/0312978 A1 | 12/2011 | Davis |
| 2012/0053190 A1 | 3/2012 | Feinberg et al. |
| 2012/0070443 A1 | 3/2012 | Movsesian |
| 2012/0071450 A1 | 3/2012 | Li et al. |
| 2012/0238589 A1 | 9/2012 | Li et al. |
| 2013/0018063 A1 | 1/2013 | Li et al. |
| 2013/0085123 A1 | 4/2013 | Li et al. |
| 2013/0331363 A1 | 12/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |
| 2014/0194396 A1 | 7/2014 | Li et al. |
| 2014/0357606 A1 | 12/2014 | Li et al. |
| 2015/0038474 A1 | 2/2015 | Li et al. |
| 2015/0072965 A1 | 3/2015 | Li et al. |
| 2015/0080357 A1 | 3/2015 | Li et al. |
| 2015/0139903 A1 | 5/2015 | Li et al. |
| 2015/0197528 A1 | 7/2015 | Li et al. |
| 2015/0259353 A1* | 9/2015 | Li .......................... C07D 487/14 514/257 |

(Continued)

FOREIGN PATENT DOCUMENTS

| | | | |
|---|---|---|---|
| WO | WO 2006/133261 | * 12/2006 | ........... A61K 31/519 |
| WO | WO 2006/133261 A2 | 12/2006 | |
| WO | WO 2008/063505 | 5/2008 | |

(Continued)

OTHER PUBLICATIONS

West, Anthony R., Solid State Chemistry and Its Applications, Wiley, New York, 1988, 358.*
International Search Report & Written Opinion of PCT/US2013/047123 issued on Dec. 6, 2013.
International Search Report & Written Opinion of PCT/US2014/043422 issued on Apr. 3, 2015.
Bowker, "A Procedure for Salt Selection and Optimization". Handbook of Pharmaceutical Salts: Properties, Selection, and Use, Chapter 7, 2002, pp. 162-173.
Lee et al., "Large-Scale Aspects of Salt Formation: Processing of Intermediates and Final Products". Handbook of Pharmaceutical Salts: Properties, Selection, and Use, Chapters 8, 2002, pp. 191-192,211-214.

(Continued)

*Primary Examiner* — Erich A Leeser
(74) *Attorney, Agent, or Firm* — Hoxie & Associates LLC

(57) ABSTRACT

The present invention relates to crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, and methods of making and using such crystals.

32 Claims, 9 Drawing Sheets

(56) References Cited

U.S. PATENT DOCUMENTS

2016/0083390 A1    3/2016  Li et al.

FOREIGN PATENT DOCUMENTS

| WO | WO 2008/070095 |      | 6/2008  |
|----|----------------|------|---------|
| WO | WO 2009/075784 |      | 6/2009  |
| WO | WO 2010/065148 |      | 6/2010  |
| WO | WO 2010/065149 |      | 6/2010  |
| WO | WO 2010/065151 |      | 6/2010  |
| WO | WO 2010/098839 |      | 9/2010  |
| WO | WO 2010/132127 |      | 11/2010 |
| WO | WO 2011/043816 |      | 4/2011  |
| WO | WO 2011/153129 |      | 12/2011 |
| WO | WO 2011/153138 |      | 12/2011 |
| WO | WO 2012/171016 |      | 12/2012 |
| WO | WO 2013/192556 |      | 12/2013 |
| WO | WO 2014/205354 | A2   | 12/2014 |

OTHER PUBLICATIONS

Stahl et al., "Monographs on Acids and Bases". Handbook of Pharmaceutical Salts: Properties, Selection, and Use, Chapters 12, 2002, 265-266, 282-283.

Bastin, "Salt Selection and Optimisation Procedures for Pharmaceutical New Chemical Entities," *Organic Process Research & Development, American Chemical Society*, vol. 4, No. 5, 2000, pp. 427-435.

Bowker, "A Procedure for Salt Selection and Optimization," *Handbook of Pharmaceutical Salts: Properties, Selection, and Use*, 2002, Chapter 7, pp. 162-173.

Caira,"Crystalline Polymorphism of Organic Compounds," *Topics in Current Chemistry*, vol. 198, 1998, pp. 160-208.

Hilfiker, "Polymorphism in the Pharmaceutical Industry," 2006, pp. 1-19.

\* cited by examiner

Figure 1-A
Differential Scanning Calorimetry (DSC) thermograph of the mono-ethanol solvate crystals
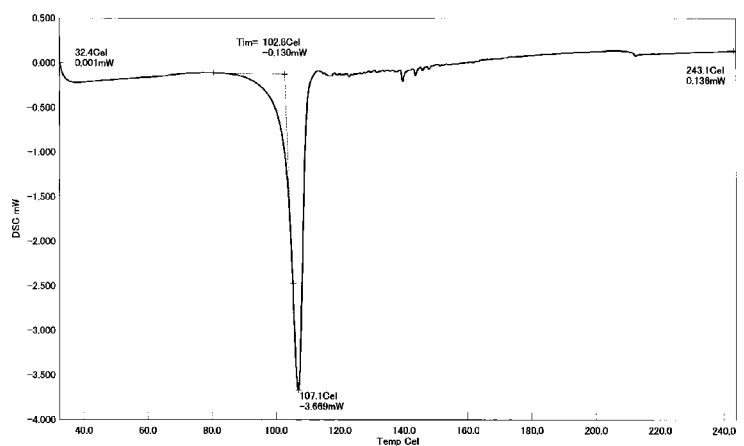
Figure 1-B
XRPD of the mono-ethanol solvate crystals
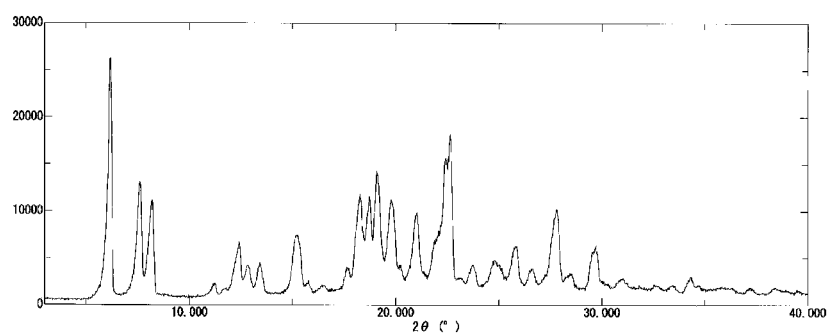

Figure 2-A
Differential Scanning Calorimetry (DSC) thermograph of the mono-*n*-propanol solvate crystals
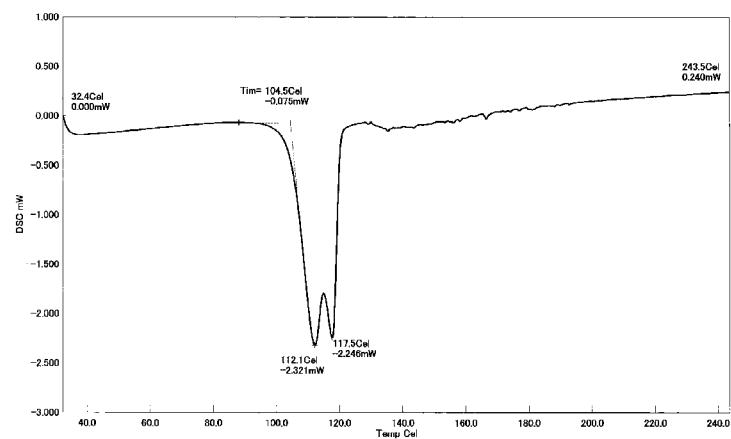
Figure 2-B
XRPD of the mono-*n*-propanol solvate crystals
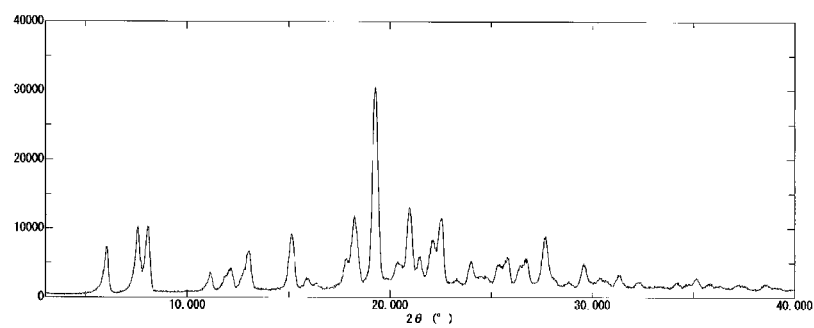

Figure 3-A
Differential Scanning Calorimetry (DSC) thermograph of the mono-2-propanol solvate crystals
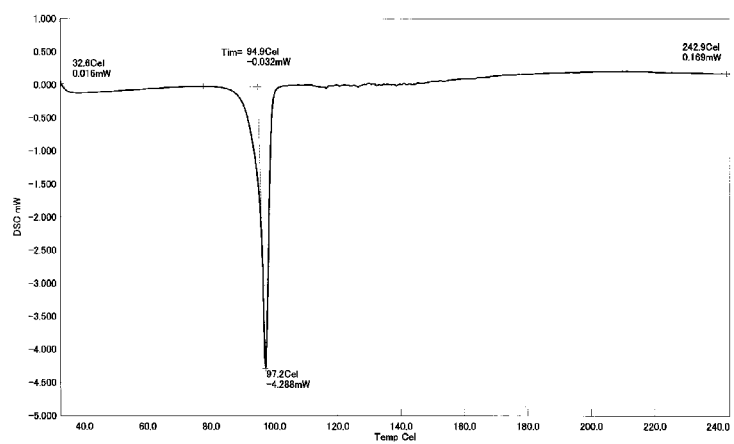
Figure 3-B
XRPD of the mono-2-propanol solvate crystals
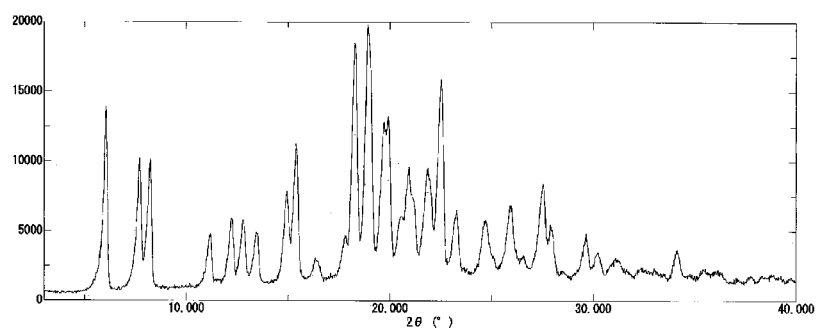

Figure 4-A
Differential Scanning Calorimetry (DSC) thermograph of the non-solvate crystals
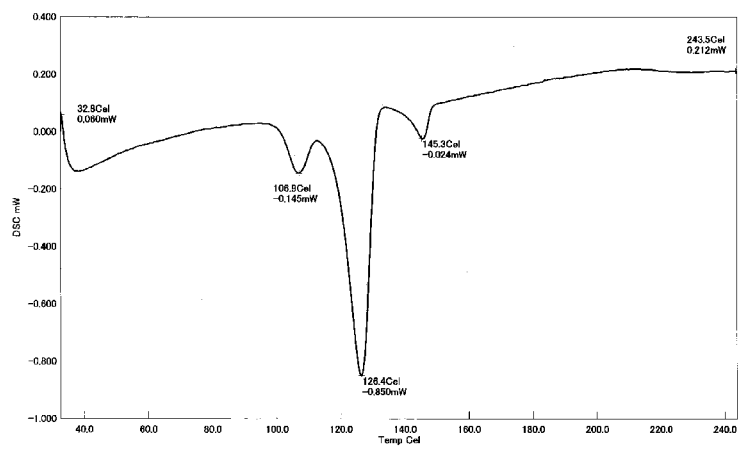
Figure 4-B
XRPD of the non-solvate crystals
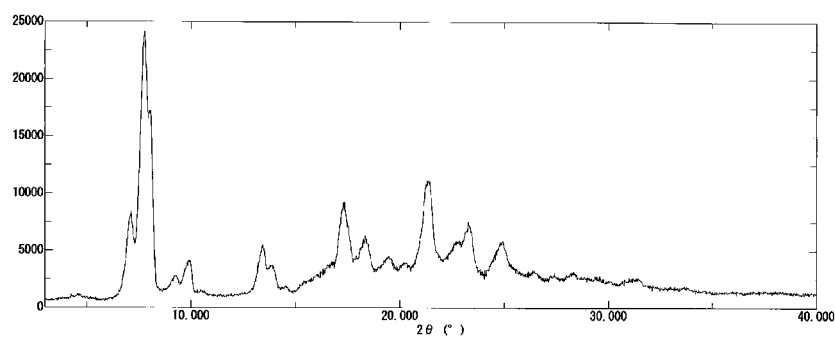

Figure 5-A
Differential Scanning Calorimetry (DSC) thermograph of the mono-methanol solvate crystals
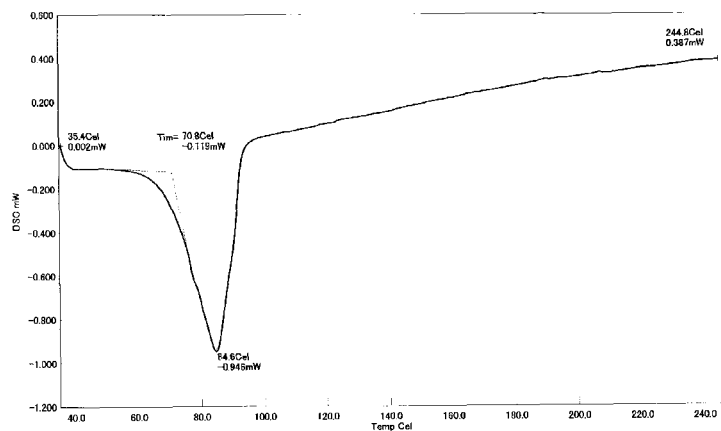
Figure 5-B
XRPD of the mono-methanol solvate crystals
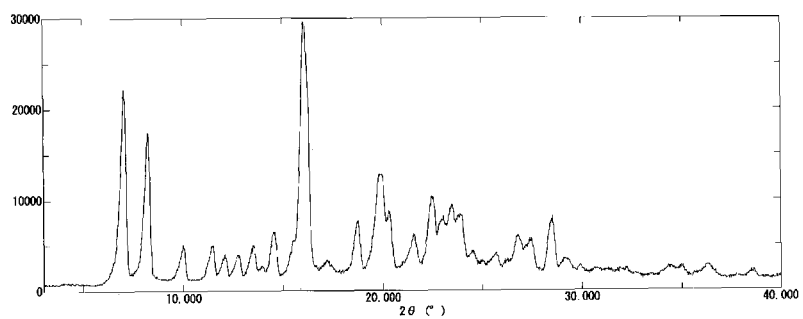

Figure 6-A
XRPD of the mono-ethanol solvate crystals
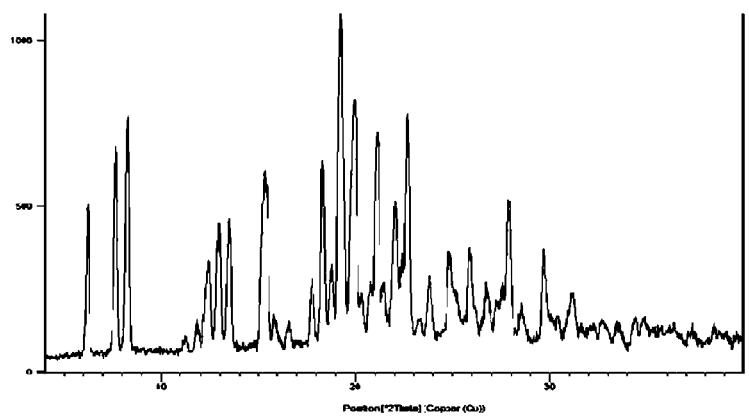
Figure 6-B
DSC andTGA of the mono-ethanol solvate crystals
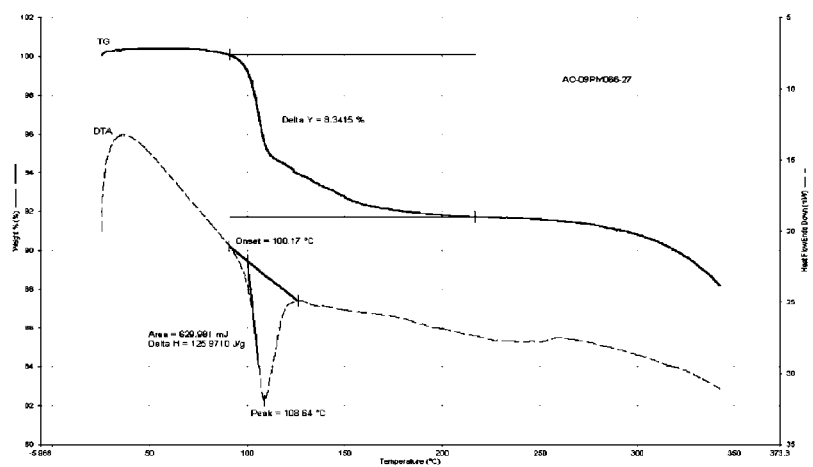

Figure 7-A
Differential Scanning Calorimetry (DSC) thermograph of the mono-n-butanol solvate crystals
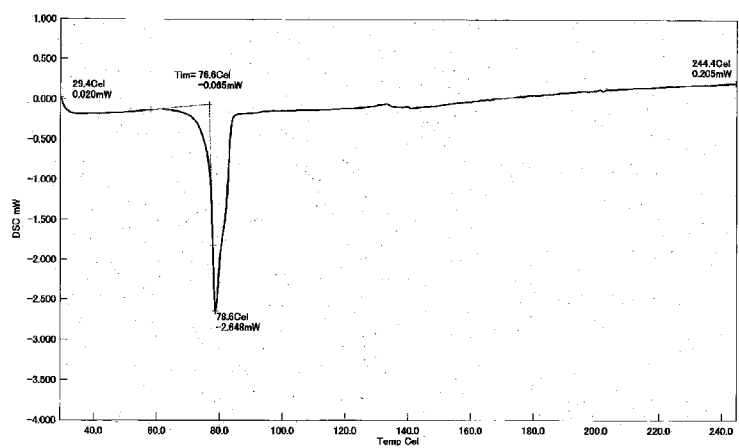
Figure 7-B
XRPD of the mono-n-butanol solvate crystals
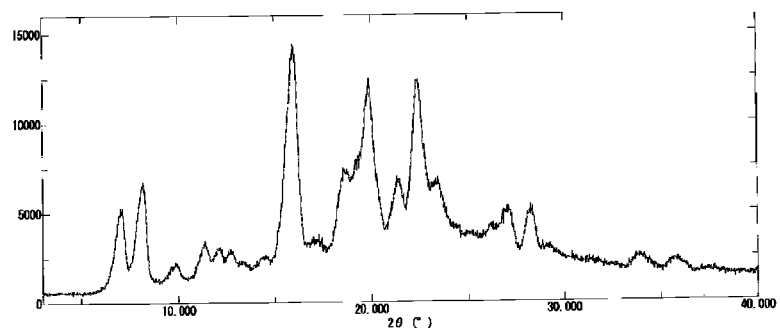

Figure 8-A
Differential Scanning Calorimetry (DSC) thermograph of hemi-fumarate 0.5 ethyl acetate 0.3 acetone solvate crystals
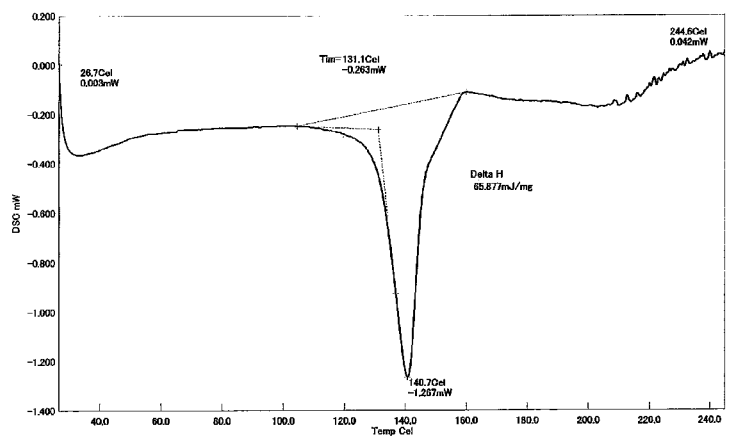
Figure 8-B
XRPD of hemi-fumarate 0.5 ethyl acetate 0.3 acetone solvate crystals
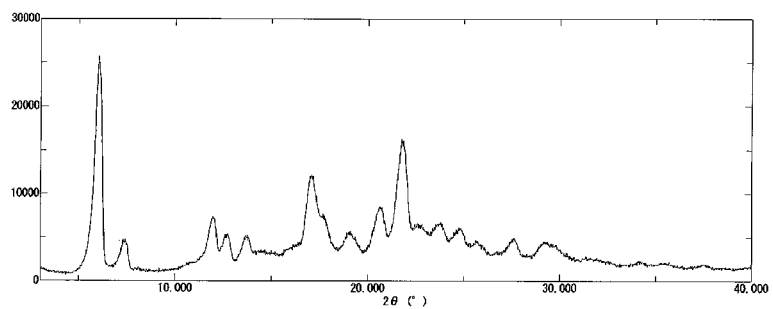

Figure 9-A
Differential Scanning Calorimetry (DSC) thermograph of the benzoate crystals
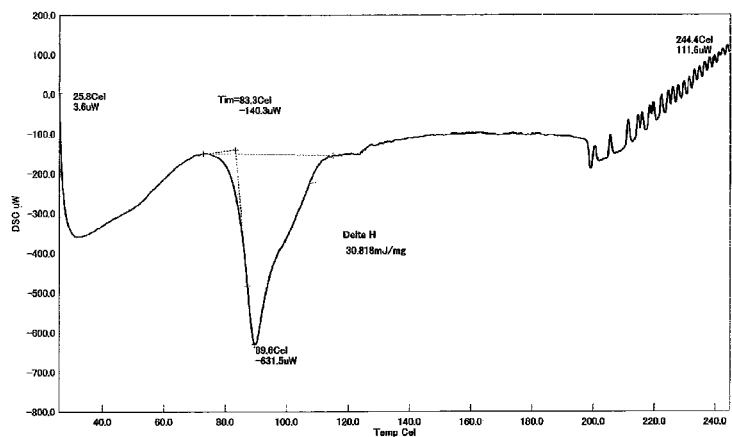
Figure 9-B
XRPD of the benzoate crystals
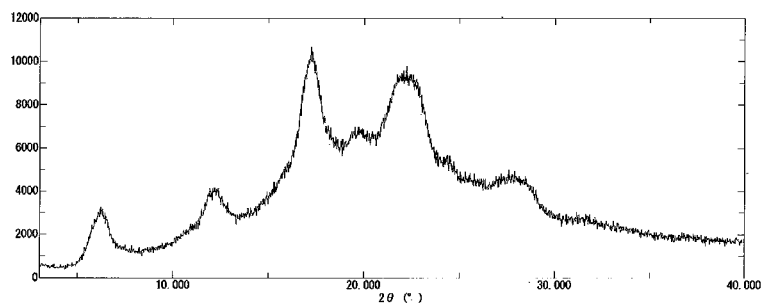

FREE BASE CRYSTALS

CROSS-REFERENCE TO RELATED APPLICATIONS

This application is a U.S. National Stage application of PCT/US2014/043422, filed on Jun. 20, 2014, which claims priority from U.S. Provisional Application 61/919,424, filed on Dec. 20, 2013, and U.S. Provisional Application 61/838,105, filed Jun. 21, 2013, the contents of each of which are herein incorporated by reference in their entirety.

FIELD OF THE INVENTION

The present invention relates to crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base, and methods of making and using such free base crystals.

BACKGROUND OF THE INVENTION

The compound (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one is disclosed in WO 2009/075784 (U.S. Pub. No. 2010/0273754). This compound has been found to be a potent and selective phosphodiesterase 1 (PDE 1) inhibitor useful for the treatment or prophylaxis of disorders characterized by low levels of cAMP and/or cGMP in cells expressing PDE1, and/or reduced dopamine D1 receptor signaling activity (e.g., Parkinson's disease, Tourette's Syndrome, Autism, fragile X syndrome, ADHD, restless leg syndrome, depression, cognitive impairment of schizophrenia, narcolepsy); and/or any disease or condition that may be ameliorated by the enhancement of progesterone signaling. This list of disorders is exemplary and not intended to be exhaustive.

The publication WO 2009/075784 generally discloses the compound (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in free base form and generally in pharmaceutically acceptable salt form. The monophosphate salt crystals of the compound (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one ("the Compound") is disclosed in U.S. Provisional Application No. 61/662,335. These applications, however, do not disclose specific crystals of the Compound in free base form and use of such free base crystals, which is now the subject of the current application.

SUMMARY OF THE INVENTION

Using a combination of twenty-four different solvents with maturation, temperature cycling, evaporation, crash cooling, anti-solvent addition, moisture induced crystallisation, annealing and ultrasound facilitated crystallization techniques, it has surprisingly been found that the Compound (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in free base form ("Compound A"), while exists as amorphous solids or oils in many solvent systems, can be isolated in crystalline form when specific solvent system and techniques are used. These free base crystals are stable and are especially advantageous in the preparation of the monophosphate salt crystals of said Compound A, the preparation of which salt crystals generally requires a very well-controlled stochiometric amount of the phosphoric acid to form a 1:1 Compound A to acid ratio. Without being bound to any particular theory, it is believed that the Compound A in free base crystalline form contains minimum impurity compared to the amorphous form, allowing the amount of phosphoric acid for the preparation of the monophosphoric acid addition salt of the Compound A to be determined accurately, thereby producing the monophosphate salt crystals efficiently, consistently and reproducibly. Therefore, in the first aspect, the invention provides the following:

1.1 Å crystal of Compound A, i.e., (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base ("free base crystal");

1.2 The free base crystal according to formula 1.1, wherein the free base crystal is in non-solvate form;

1.3 The free base crystal according to formula 1.1, wherein the free base crystal is in solvate form;

1.4 The free base crystal according to formula 1.3, wherein the free base crystal is in solvate form with alcohol;

1.5 The free base crystal according to formula 1.4, wherein the free base crystal is in solvate form with methanol, ethanol, propanol (e.g., n-propanol or iso-propanol) or butanol (e.g., n-butanol);

1.6 The free base crystal according to any of formulae 1.1-1.5, wherein the free base crystal is in non-hydrate or hydrate form;

1.7 The free base crystal according to any of formulae 1.4-1.6, wherein said free base crystal exhibits an X-ray powder diffraction pattern comprising at least five peaks having 2-theta angle values selected from the group consisting of 6.2, 7.6, 8.2, 11.2, 12.4, 12.8, 13.4, 15.2, 16.5, 17.6, 18.2, 19.1, 19.8, 21.0, 21.9, 22.6, 23.1, 23.7, 24.8, 25.8, 26.6, 27.8, 28.4, 29.6, 30.9, 31.8, 32.6, 33.4, 34.3, 36.3, 37.2, 38.4 and 39.5 degrees, wherein the XRPD pattern is measured in a diffractometer using copper anode, e.g., at wavelength alpha1 of 1.5406 Å and wavelength alpha2 of 1.5444 Å;

1.8 The free base crystal according to any of formulae 1.4-1.6, wherein said free base crystal exhibits an X-ray powder diffraction pattern comprising at least five peaks having d-spacing values selected from the group consisting of 14.34, 11.65, 10.83, 7.91, 7.16, 6.89, 6.59, 5.82, 5.37, 5.03, 4.87, 4.64, 4.48, 4.23, 4.06, 3.93, 3.85, 3.75, 3.59, 3.45, 3.35, 3.21, 3.14, 3.01, 2.89, 2.81, 2.74, 2.68, 2.61, 2.47, 2.42, 2.34 and 2.28 Å;

1.9 The free base crystal according to any of formulae 1.4-1.6, wherein said free base crystal exhibits an X-ray powder diffraction pattern comprising at least five peaks having d-spacing values selected from the group consisting of 14.34, 11.65, 10.83, 5.82, 4.87, 4.64, 4.48, 4.23, 3.93 and 3.21 Å;

1.10 The free base crystal according to any of formulae 1.4-1.6, wherein said free base crystal exhibits an X-ray powder diffraction pattern comprising at least five peaks having 2-theta angle and/or d-spacing values selected from those set forth in Table 1 below:

TABLE 1

| No | Pos. [°2Th.] | d-spacing [Å] | Height [cps] | Rel. Int. [%] |
|---|---|---|---|---|
| 1 | 6.16 | 14.3361 | 15985 | 100 |
| 2 | 7.58 | 11.6533 | 7985 | 50 |
| 3 | 8.16 | 10.8263 | 6641 | 42 |
| 4 | 11.18 | 7.9077 | 890 | 6 |
| 5 | 12.36 | 7.1553 | 3411 | 22 |
| 6 | 12.84 | 6.8888 | 2076 | 13 |
| 7 | 13.42 | 6.5924 | 2257 | 15 |
| 8 | 15.20 | 5.8241 | 4004 | 26 |
| 9 | 16.48 | 5.3746 | 433 | 3 |
| 10 | 17.62 | 5.0293 | 1692 | 11 |
| 11 | 18.22 | 4.8650 | 6533 | 41 |
| 12 | 19.10 | 4.6428 | 8513 | 54 |
| 13 | 19.78 | 4.4847 | 6436 | 41 |
| 14 | 20.98 | 4.2308 | 5242 | 33 |
| 15 | 21.90 | 4.0551 | 3182 | 20 |
| 16 | 22.58 | 3.9345 | 9727 | 61 |
| 17 | 23.10 | 3.8471 | 751 | 5 |
| 18 | 23.72 | 3.7479 | 1621 | 11 |
| 19 | 24.78 | 3.5900 | 2058 | 13 |
| 20 | 25.78 | 3.4529 | 2825 | 18 |
| 21 | 26.56 | 3.3533 | 1085 | 7 |
| 22 | 27.76 | 3.2110 | 5312 | 34 |
| 23 | 28.44 | 3.1357 | 1078 | 7 |
| 24 | 29.64 | 3.0115 | 2655 | 17 |
| 25 | 30.94 | 2.8878 | 807 | 6 |
| 26 | 31.82 | 2.8099 | 352 | 3 |
| 27 | 32.60 | 2.7445 | 321 | 2 |
| 28 | 33.40 | 2.6805 | 411 | 3 |
| 29 | 34.26 | 2.6152 | 951 | 6 |
| 30 | 36.28 | 2.4741 | 278 | 2 |
| 31 | 37.18 | 2.4162 | 302 | 2 |
| 32 | 38.36 | 2.3446 | 384 | 3 |
| 33 | 39.52 | 2.2784 | 224 | 2 | wherein the XRPD pattern is measured in a diffractometer using copper anode, e.g., at wavelength alpha1 of 1.5406 Å and wavelength alpha2 of 1.5444 Å;

1.11 The free base crystal according to any of formulae 1.4-1.6, wherein said free base crystal exhibits an X-ray powder diffraction pattern comprising at least five peaks having 2-theta angle and/or d-spacing values selected from those set forth in Table 1-A below:

TABLE 1-A

| Pos. [°2Th.] | d-spacing [Å] | Height [cps] | Rel. Int. [%] |
|---|---|---|---|
| 6.16 | 14.3361 | 15985 | 100 |
| 7.58 | 11.6533 | 7985 | 50 |
| 8.16 | 10.8263 | 6641 | 42 |
| 15.20 | 5.8241 | 4004 | 26 |
| 18.22 | 4.8650 | 6533 | 41 |
| 19.10 | 4.6428 | 8513 | 54 |
| 19.78 | 4.4847 | 6436 | 41 |
| 20.98 | 4.2308 | 5242 | 33 |
| 22.58 | 3.9345 | 9727 | 61 |
| 27.76 | 3.2110 | 5312 | 34 | wherein the XRPD pattern is measured in a diffractometer using copper anode, e.g., at wavelength alpha1 of 1.5406 Å and wavelength alpha2 of 1.5444 Å;

1.12 The free base crystal according to any of formulae 1.4-1.11, wherein said free base crystal exhibits an X-ray powder diffraction pattern corresponding with or substantially as depicted in FIG. 1-B or 6-A;

1.13 The free base crystal according to any of formulae 1.4-1.12, wherein said free base crystal exhibits a Differential Scanning calorimetry (DSC) pattern comprising an endothermic peak at about 107° C.-108° C.;

1.14 The free base crystal according to formula 1.13, wherein the crystal exhibits a Differential Scanning calorimetry (DSC) pattern corresponding with or substantially as depicted in FIG. 1-A or 6-B;

1.15 The free base crystal according to any of formulae 1.4-1.6, wherein said free base crystal exhibits an X-ray powder diffraction pattern comprising at least five peaks having 2-theta angle values selected from the group consisting of 6.0, 7.6, 8.1, 11.1, 12.0, 12.1, 13.0, 15.1, 15.9, 16.3, 18.2, 19.3, 20.4, 21.0, 21.5, 22.1, 22.5, 23.3, 24.0, 25.3, 25.8, 26.7, 27.6, 28.8, 29.6, 30.3, 30.7, 31.3, 32.3, 34.1, 35.1, 35.8, 37.2 and 38.5 degrees, wherein the XRPD pattern is measured in a diffractometer using copper anode, e.g., at wavelength alpha1 of 1.5406 Å and wavelength alpha2 of 1.5444 Å;

1.16 The free base crystal according to any of formulae 1.4-1.6, wherein said free base crystal exhibits an X-ray powder diffraction pattern comprising at least five peaks having d-spacing values selected from the group consisting of 14.67, 11.68, 10.96, 7.95, 7.39, 7.30, 6.80, 5.85, 5.57, 5.42, 4.86, 4.60, 4.36, 4.23, 4.14, 4.03, 3.95, 3.82, 3.71, 3.51, 3.46, 3.34, 3.22, 3.10, 3.02, 2.94, 2.91, 2.86, 2.77, 2.62, 2.55, 2.51, 2.42 and 2.33 Å;

1.17 The free base crystal according to any of formulae 1.4-1.6, wherein said free base crystal exhibits an X-ray powder diffraction pattern comprising at least five peaks having d-spacing values selected from the group consisting of 14.67, 11.68, 10.96, 5.85, 4.86, 4.60, 4.23, 4.03, 3.95 and 3.22 Å.

1.18 The free base crystal according to any of formulae 1.4-1.6, wherein said free base crystal exhibits an X-ray powder diffraction pattern comprising at least five peaks having 2-theta angle and/or d-spacing values selected from those set forth in Table 2 below:

TABLE 2

| No | Pos. [°2Th.] | d-spacing [Å] | Height [cps] | Rel. Int. [%] |
|---|---|---|---|---|
| 1 | 6.02 | 14.6692 | 4134 | 22 |
| 2 | 7.56 | 11.6841 | 6333 | 33 |
| 3 | 8.06 | 10.9604 | 6419 | 33 |
| 4 | 11.12 | 7.9502 | 1717 | 9 |
| 5 | 11.96 | 7.3937 | 1495 | 8 |
| 6 | 12.12 | 7.2964 | 2064 | 11 |
| 7 | 13.00 | 6.8044 | 3750 | 20 |
| 8 | 15.14 | 5.8471 | 5302 | 28 |
| 9 | 15.90 | 5.5693 | 958 | 5 |
| 10 | 16.34 | 5.4203 | 458 | 3 |
| 11 | 18.24 | 4.8597 | 6917 | 36 |
| 12 | 19.26 | 4.6046 | 19500 | 100 |
| 13 | 20.36 | 4.3582 | 2351 | 13 |
| 14 | 20.96 | 4.2348 | 7782 | 40 |
| 15 | 21.46 | 4.1373 | 2813 | 15 |
| 16 | 22.06 | 4.0261 | 4378 | 23 |
| 17 | 22.50 | 3.9483 | 6583 | 34 |
| 18 | 23.26 | 3.8210 | 547 | 3 |
| 19 | 23.96 | 3.7109 | 2333 | 12 |
| 20 | 25.32 | 3.5146 | 2052 | 11 |
| 21 | 25.76 | 3.4556 | 2554 | 14 |
| 22 | 26.70 | 3.3360 | 2694 | 14 |
| 23 | 27.64 | 3.2247 | 4917 | 26 |
| 24 | 28.80 | 3.0974 | 394 | 3 |
| 25 | 29.56 | 3.0194 | 2188 | 12 |
| 26 | 30.34 | 2.9436 | 867 | 5 |
| 27 | 30.66 | 2.9136 | 584 | 3 |
| 28 | 31.28 | 2.8572 | 1166 | 6 |
| 29 | 32.26 | 2.7726 | 466 | 3 |
| 30 | 34.14 | 2.6241 | 549 | 3 |
| 31 | 35.12 | 2.5531 | 970 | 5 |
| 32 | 35.78 | 2.5075 | 403 | 3 |
| 33 | 37.16 | 2.4175 | 346 | 2 |
| 34 | 38.54 | 2.3340 | 403 | 3 | wherein the XRPD pattern is measured in a diffractometer using copper anode, e.g., at wavelength alpha1 of 1.5406 Å and wavelength alpha2 of 1.5444 Å;

1.19 The free base crystal according to any of formulae 1.4-1.6, wherein said free base crystal exhibits an X-ray powder diffraction pattern comprising at least five peaks having 2-theta angle and/or d-spacing values selected from those set forth in Table 2-A below:

TABLE 2-A

| Pos. [°2Th.] | d-spacing [Å] | Height [cps] | Rel. Int. [%] |
|---|---|---|---|
| 6.02 | 14.6692 | 4134 | 22 |
| 7.56 | 11.6841 | 6333 | 33 |
| 8.06 | 10.9604 | 6419 | 33 |
| 15.14 | 5.8471 | 5302 | 28 |
| 18.24 | 4.8597 | 6917 | 36 |
| 19.26 | 4.6046 | 19500 | 100 |
| 20.96 | 4.2348 | 7782 | 40 |
| 22.06 | 4.0261 | 4378 | 23 |
| 22.50 | 3.9483 | 6583 | 34 |
| 27.64 | 3.2247 | 4917 | 26 | wherein the XRPD pattern is measured in a diffractometer using copper anode, e.g., at wavelength alpha1 of 1.5406 Å and wavelength alpha2 of 1.5444 Å;

1.20 The free base crystal according to any of formulae 1.4-1.6 or 1.15-1.19, wherein the free base crystal exhibits an X-ray powder diffraction pattern corresponding with or substantially as depicted in FIG. 2-B;

1.21 The free base crystal according to any of formulae 1.4-1.6 or 1.15-1.20, wherein said free base crystal exhibits a Differential Scanning calorimetry (DSC) pattern comprising an endothermic peak between the range of 112-118° C., e.g., at 112° C. or 118° C.;

1.22 The free base crystal according to any of formulae 1.4-1.6 or 1.15-1.21, wherein the free base crystal exhibits a Differential Scanning calorimetry (DSC) pattern corresponding with or substantially as depicted in FIG. 2-A;

1.23 The free base crystal according to any of formulae 1.4-1.6, wherein said free base crystal exhibits an X-ray powder diffraction pattern comprising at least five peaks having 2-theta angle values selected from the group consisting of 6.0, 7.7, 8.2, 11.1, 12.2, 12.8, 13.4, 14.9, 15.4, 16.4, 18.2, 18.9, 19.8, 20.5, 20.9, 21.9, 22.5, 23.2, 24.7, 25.9, 26.5, 27.5, 27.9, 29.6, 30.2, 31.1, 32.3, 33.0, 34.1, 34.7, 35.4, 36.2, 37.7, 38.3 and 38.8 degrees, wherein the XRPD pattern is measured in a diffractometer using copper anode, e.g., at wavelength alpha1 of 1.5406 Å and wavelength alpha2 of 1.5444 Å;

1.24 The free base crystal according to any of formulae 1.4-1.6, wherein said free base crystal exhibits an X-ray powder diffraction pattern comprising at least five peaks having d-spacing values selected from the group consisting of 14.67, 11.53, 10.80, 7.95, 7.25, 6.93, 6.59, 5.95, 5.76, 5.41, 4.86, 4.68, 4.47, 4.33, 4.24, 4.06, 3.95, 3.82, 3.61, 3.44, 3.36, 3.25, 3.19, 3.02, 2.96, 2.87, 2.77, 2.71, 2.63, 2.58, 2.53, 2.48, 2.38, 2.35 and 2.32 Å;

1.25 The free base crystal according to any of formulae 1.4-1.6, wherein said free base crystal exhibits an X-ray powder diffraction pattern comprising at least five peaks having d-spacing values selected from the group consisting of 14.67, 11.53, 10.80, 5.76, 4.86, 4.68, 4.47, 4.24, 4.06 and 3.95 Å;

1.26 The free base crystal according to any of formulae 1.4-1.6, wherein said free base crystal exhibits an X-ray powder diffraction pattern comprising at least five peaks having 2-theta angle and/or d-spacing values selected from those set forth in Table 3 below:

TABLE 3

| No | Pos. [°2Th.] | d-spacing [Å] | Height [cps] | Rel. Int. [%] |
|---|---|---|---|---|
| 1 | 6.02 | 14.6692 | 8237 | 71 |
| 2 | 7.66 | 11.5318 | 5866 | 51 |
| 3 | 8.18 | 10.7998 | 5708 | 49 |
| 4 | 11.12 | 7.9502 | 2294 | 20 |
| 5 | 12.20 | 7.2487 | 3111 | 27 |
| 6 | 12.76 | 6.9318 | 2968 | 26 |
| 7 | 13.42 | 6.5924 | 2363 | 21 |
| 8 | 14.88 | 5.9487 | 4043 | 35 |
| 9 | 15.36 | 5.7638 | 6270 | 54 |
| 10 | 16.36 | 5.4137 | 913 | 8 |
| 11 | 18.24 | 4.8597 | 11094 | 95 |
| 12 | 18.94 | 4.6817 | 11691 | 100 |
| 13 | 19.84 | 4.4713 | 7080 | 61 |
| 14 | 20.50 | 4.3288 | 2855 | 25 |
| 15 | 20.92 | 4.2428 | 5215 | 45 |
| 16 | 21.86 | 4.0625 | 5015 | 43 |
| 17 | 22.48 | 3.9518 | 9259 | 80 |
| 18 | 23.22 | 3.8275 | 2798 | 24 |
| 19 | 24.66 | 3.6072 | 2542 | 22 |
| 20 | 25.90 | 3.4372 | 3343 | 29 |
| 21 | 26.54 | 3.3558 | 918 | 8 |
| 22 | 27.46 | 3.2454 | 4116 | 36 |
| 23 | 27.92 | 3.1929 | 2252 | 20 |
| 24 | 29.60 | 3.0154 | 1911 | 17 |
| 25 | 30.18 | 2.9588 | 1085 | 10 |
| 26 | 31.12 | 2.8715 | 837 | 8 |
| 27 | 32.30 | 2.7693 | 493 | 5 |
| 28 | 33.02 | 2.7105 | 536 | 5 |
| 29 | 34.10 | 2.6271 | 1400 | 12 |
| 30 | 34.70 | 2.5830 | 251 | 3 |
| 31 | 35.42 | 2.5322 | 568 | 5 |
| 32 | 36.22 | 2.4780 | 371 | 4 |
| 33 | 37.72 | 2.3829 | 209 | 2 |
| 34 | 38.30 | 2.3481 | 296 | 3 |
| 35 | 38.82 | 2.3178 | 304 | 3 | wherein the XRPD pattern is measured in a diffractometer using copper anode, e.g., at wavelength alpha1 of 1.5406 Å and wavelength alpha2 of 1.5444 Å;

1.27 The free base crystal according to any of formulae 1.4-1.6, wherein said free base crystal exhibits an X-ray powder diffraction pattern comprising at least five peaks having 2-theta angle and/or d-spacing values selected from those set forth in Table 3-A below:

TABLE 3-A

| Pos. [°2Th.] | d-spacing [Å] | Height [cps] | Rel. Int. [%] |
|---|---|---|---|
| 6.02 | 14.6692 | 8237 | 71 |
| 7.66 | 11.5318 | 5866 | 51 |
| 8.18 | 10.7998 | 5708 | 49 |
| 15.36 | 5.7638 | 6270 | 54 |
| 18.24 | 4.8597 | 11094 | 95 |
| 18.94 | 4.6817 | 11691 | 100 |
| 19.84 | 4.4713 | 7080 | 61 |
| 20.92 | 4.2428 | 5215 | 45 |
| 21.86 | 4.0625 | 5015 | 43 |
| 22.48 | 3.9518 | 9259 | 80 | wherein the XRPD pattern is measured in a diffractometer using copper anode, e.g., at wavelength alpha1 of 1.5406 Å and wavelength alpha2 of 1.5444 Å;

1.28 The free base crystal according to any of formulae 1.4-1.6 or 1.23-1.27, wherein said free base crystal exhibits an X-ray powder diffraction pattern corresponding with or substantially as depicted in FIG. 3-B;

1.29 The free base crystal according to any of formulae 1.4-1.6 or 1.23-1.28, wherein said free base crystal exhibits a Differential Scanning calorimetry (DSC) pattern comprising an endothermic peak at about 97° C.;

1.30 The free base crystal according to any of formulae 1.4-1.6 or 1.23-1.29, wherein said free base crystal exhibits a Differential Scanning calorimetry (DSC) pattern corresponding with or substantially as depicted in FIG. 3-A;

1.31 The free base crystal according to any of formulae 1.1-1.2, 1.6, wherein said free base crystal exhibits an X-ray powder diffraction pattern comprising at least five peaks having 2-theta angle values selected from the group consisting of 4.6, 7.1, 7.7, 8.0, 9.2, 9.9, 10.5, 13.4, 13.9, 14.5, 15.4, 16.6, 17.3, 18.3, 19.4, 20.2, 21.3, 22.7, 23.3, 24.9, 26.4, 27.3, 28.3, 29.4, 30.0, 31.2 and 31.4 degrees, wherein the XRPD pattern is measured in a diffractometer using copper anode, e.g., at wavelength alpha1 of 1.5406 Å and wavelength alpha2 of 1.5444 Å;

1.32 The free base crystal according to any of formulae 1.1-1.2, 1.6, wherein said free base crystal exhibits an X-ray powder diffraction pattern comprising at least five peaks having d-spacing values selected from the group consisting of 19.11, 12.51, 11.41, 11.01, 9.58, 8.95, 8.40, 6.60, 6.37, 6.10, 5.74, 5.33, 5.13, 4.83, 4.56, 4.39, 4.16, 3.91, 3.81, 3.58, 3.37, 3.26, 3.15, 3.03, 2.97, 2.87 and 2.84 Å;

1.33 The free base crystal according to any of formulae 1.1-1.2, 1.6, wherein said free base crystal exhibits an X-ray powder diffraction pattern comprising at least five peaks having d-spacing values selected from the group consisting of 12.51, 11.41, 11.01, 9.58, 8.95, 6.60, 5.13, 4.16 and 3.81 Å;

1.34 The free base crystal according to any of formulae 1.1-1.2, 1.6, wherein said free base crystal exhibits an X-ray powder diffraction pattern comprising at least five peaks having 2-theta angle and/or d-spacing values selected from those set forth in Table 4 below:

TABLE 4

| No | Pos. [°2Th.] | d-spacing [Å] | Height [cps] | Rel. Int. [%] |
|---|---|---|---|---|
| 1 | 4.62 | 19.1107 | 273 | 2 |
| 2 | 7.06 | 12.5104 | 4683 | 31 |
| 3 | 7.74 | 11.4128 | 15123 | 100 |
| 4 | 8.02 | 11.0149 | 10678 | 71 |
| 5 | 9.22 | 9.5838 | 1208 | 8 |
| 6 | 9.88 | 8.9451 | 2099 | 14 |
| 7 | 10.52 | 8.4023 | 289 | 2 |
| 8 | 13.40 | 6.6022 | 2653 | 18 |
| 9 | 13.88 | 6.3749 | 1553 | 11 |
| 10 | 14.52 | 6.0953 | 305 | 3 |
| 11 | 15.42 | 5.7415 | 511 | 4 |
| 12 | 16.62 | 5.3296 | 1391 | 10 |
| 13 | 17.28 | 5.1275 | 4822 | 32 |
| 14 | 18.34 | 4.8335 | 2675 | 18 |
| 15 | 19.44 | 4.5624 | 1600 | 11 |
| 16 | 20.20 | 4.3924 | 1250 | 9 |
| 17 | 21.34 | 4.1603 | 6007 | 40 |
| 18 | 22.70 | 3.9140 | 2330 | 16 |
| 19 | 23.30 | 3.8145 | 3311 | 22 |
| 20 | 24.88 | 3.5758 | 2363 | 16 |
| 21 | 26.44 | 3.3682 | 627 | 5 |
| 22 | 27.32 | 3.2617 | 441 | 3 |
| 23 | 28.28 | 3.1531 | 667 | 5 |
| 24 | 29.42 | 3.0335 | 393 | 3 |
| 25 | 30.04 | 2.9723 | 269 | 2 |
| 26 | 31.18 | 2.8661 | 433 | 3 |
| 27 | 31.42 | 2.8448 | 515 | 4 | wherein the XRPD pattern is measured in a diffractometer using copper anode, e.g., at wavelength alpha1 of 1.5406 Å and wavelength alpha2 of 1.5444 Å;

1.35 The free base crystal according to any of formulae 1.1-1.2, 1.6, wherein said free base crystal exhibits an X-ray powder diffraction pattern comprising at least five peaks having 2-theta angle and/or d-spacing values selected from those set forth in Table 4-A below:

TABLE 4-A

| Pos. [°2Th.] | d-spacing [Å] | Height [cps] | Rel. Int. [%] |
|---|---|---|---|
| 7.06 | 12.5104 | 4683 | 31 |
| 7.74 | 11.4128 | 15123 | 100 |
| 8.02 | 11.0149 | 10678 | 71 |
| 9.22 | 9.5838 | 1208 | 8 |
| 9.88 | 8.9451 | 2099 | 14 |
| 13.40 | 6.6022 | 2653 | 18 |
| 17.28 | 5.1275 | 4822 | 32 |
| 21.34 | 4.1603 | 6007 | 40 |
| 23.30 | 3.8145 | 3311 | 22 | wherein the XRPD pattern is measured in a diffractometer using copper anode, e.g., at wavelength alpha1 of 1.5406 Å and wavelength alpha2 of 1.5444 Å;

1.36 The free base crystal according to any of formulae 1.1-1.2, 1.6 or 1.31-1.35, wherein said free base crystal exhibits an X-ray powder diffraction pattern corresponding with or substantially as depicted in FIG. 4-B;

1.37 The free base crystal according to any of formulae 1.1-1.2, 1.6 or 1.31-1.36, wherein said free base crystal exhibits a Differential Scanning calorimetry (DSC) pattern comprising an endothermic peak at about 126° C.;

1.38 The free base crystal according to any of formulae 1.1-1.2, 1.6 or 1.31-1.37, wherein said free base crystal exhibits a Differential Scanning calorimetry (DSC) pattern corresponding with or substantially as depicted in FIG. 4-A;

1.39 The free base crystal according to any of formulae 1.4-1.6, wherein said free base crystal exhibits an X-ray powder diffraction pattern comprising at least five peaks having 2-theta angle values selected from the group consisting of 7.0, 8.2, 9.9, 11.4, 12.0, 12.7, 13.5, 14.5, 16.1, 17.2, 18.7, 19.9, 21.5, 22.4, 22.9, 23.4, 23.9, 24.5, 25.6, 26.8, 27.4, 28.4, 29.2, 29.9, 30.7, 31.3, 31.9, 32.2, 34.4, 35.0, 36.3 and 38.6 degrees, wherein the XRPD pattern is measured in a diffractometer using copper anode, e.g., at wavelength alpha1 of 1.5406 Å and wavelength alpha2 of 1.5444 Å;

1.40 The free base crystal according to any of formulae 1.4-1.6, wherein said free base crystal exhibits an X-ray powder diffraction pattern comprising at least five peaks having d-spacing values selected from the group consisting of 12.58, 10.75, 8.89, 7.76, 7.36, 6.95, 6.57, 6.10, 5.50, 5.16, 4.74, 4.47, 4.12, 3.96, 3.87, 3.80, 3.72, 3.63, 3.47, 3.33, 3.25, 3.14, 3.06, 2.99, 2.91, 2.86, 2.81, 2.78, 2.61, 2.56, 2.47 and 2.33 Å;

1.41 The free base crystal according to any of formulae 1.4-1.6, wherein said free base crystal exhibits an X-ray powder diffraction pattern comprising at least five peaks having d-spacing values selected from the group consisting of 12.58, 10.75, 5.50, 4.74, 4.47, 3.96, 3.87, 3.80, 3.72 and 3.14 Å;

1.42 The free base crystal according to any of formulae 1.4-1.6, wherein said free base crystal exhibits an X-ray powder diffraction pattern comprising at least five peaks having 2-theta angle and/or d-spacing values selected from those set forth in Table 5 below:

TABLE 5

| No | Pos. [°2Th.] | d-spacing [Å] | Height [cps] | Rel. Int. [%] |
|---|---|---|---|---|
| 1 | 7.02 | 12.5816 | 13378 | 75 |
| 2 | 8.22 | 10.7474 | 10588 | 59 |
| 3 | 9.94 | 8.8912 | 2364 | 14 |
| 4 | 11.40 | 7.7556 | 2380 | 14 |
| 5 | 12.02 | 7.3569 | 1560 | 9 |
| 6 | 12.72 | 6.9536 | 1637 | 10 |
| 7 | 13.46 | 6.5729 | 2246 | 13 |
| 8 | 14.52 | 6.0953 | 3243 | 18 |
| 9 | 16.10 | 5.5005 | 18007 | 100 |
| 10 | 17.18 | 5.1571 | 922 | 6 |
| 11 | 18.72 | 4.7362 | 3803 | 22 |
| 12 | 19.86 | 4.4668 | 7203 | 40 |
| 13 | 21.54 | 4.1221 | 2741 | 16 |
| 14 | 22.44 | 3.9588 | 5449 | 31 |
| 15 | 22.94 | 3.8736 | 3705 | 21 |
| 16 | 23.42 | 3.7953 | 4840 | 27 |
| 17 | 23.90 | 3.7201 | 4152 | 24 |
| 18 | 24.48 | 3.6333 | 1443 | 9 |
| 19 | 25.64 | 3.4715 | 1382 | 8 |
| 20 | 26.76 | 3.3287 | 2692 | 15 |
| 21 | 27.42 | 3.2500 | 2463 | 14 |
| 22 | 28.44 | 3.1357 | 3887 | 22 |
| 23 | 29.16 | 3.0599 | 1027 | 6 |
| 24 | 29.88 | 2.9878 | 603 | 4 |
| 25 | 30.68 | 2.9117 | 365 | 3 |
| 26 | 31.30 | 2.8554 | 329 | 2 |
| 27 | 31.86 | 2.8065 | 446 | 3 |
| 28 | 32.16 | 2.7810 | 477 | 3 |
| 29 | 34.38 | 2.6063 | 665 | 4 |
| 30 | 34.98 | 2.5630 | 856 | 5 |
| 31 | 36.32 | 2.4715 | 961 | 6 |
| 32 | 38.56 | 2.3329 | 448 | 3 | wherein the XRPD pattern is measured in a diffractometer using copper anode, e.g., at wavelength alpha1 of 1.5406 Å and wavelength alpha2 of 1.5444 Å;

1.43 The free base crystal according to any of formulae 1.4-1.6, wherein said free base crystal exhibits an X-ray powder diffraction pattern comprising at least five peaks having 2-theta angle and/or d-spacing values selected from those set forth in Table 5-A below:

TABLE 5-A

| No | Pos. [°2Th.] | d-spacing [Å] | Height [cps] | Rel. Int. [%] |
|---|---|---|---|---|
| 1 | 7.02 | 12.5816 | 13378 | 75 |
| 2 | 8.22 | 10.7474 | 10588 | 59 |
| 9 | 16.10 | 5.5005 | 18007 | 100 |
| 11 | 18.72 | 4.7362 | 3803 | 22 |
| 12 | 19.86 | 4.4668 | 7203 | 40 |
| 14 | 22.44 | 3.9588 | 5449 | 31 |
| 15 | 22.94 | 3.8736 | 3705 | 21 |
| 16 | 23.42 | 3.7953 | 4840 | 27 |
| 17 | 23.90 | 3.7201 | 4152 | 24 |
| 22 | 28.44 | 3.1357 | 3887 | 22 | wherein the XRPD pattern is measured in a diffractometer using copper anode, e.g., at wavelength alpha1 of 1.5406 Å and wavelength alpha2 of 1.5444 Å;

1.44 The free base crystal according to any of formulae 1.4-1.6 or 1.39-1.43, wherein said free base crystal exhibits an X-ray powder diffraction pattern corresponding with or substantially as depicted in FIG. 5-B;

1.45 The free base crystal according to any of formulae 1.4-1.6 or 1.39-1.44, wherein said free base crystal exhibits a Differential Scanning calorimetry (DSC) pattern comprising an endothermic peak at about 84-85° C., for example about 84.6° C.; or a Differential Scanning calorimetry (DSC) pattern corresponding with or substantially as depicted in FIG. 5-A;

1.46 The free base crystal according to any of formulae 1.4-1.6, wherein said free base crystal exhibits an X-ray powder diffraction pattern comprising at least five peaks having 2-theta angle values selected from the group consisting of 7.1, 8.2, 9.9, 11.4, 12.1, 12.8, 13.4, 14.4, 16.0, 17.3, 18.6, 19.9, 21.4, 22.4, 23.4, 24.4, 25.3, 26.2, 27.1, 28.3, 29.2, 33.8, 34.0, 35.8 and 36.3 degrees, wherein the XRPD pattern is measured in a diffractometer using copper anode, e.g., at wavelength alpha1 of 1.5406 Å and wavelength alpha2 of 1.5444 Å;

1.47 The free base crystal according to any of formulae 1.4-1.6, wherein said free base crystal exhibits an X-ray powder diffraction pattern comprising at least five peaks having d-spacing values selected from the group consisting of 12.51, 10.80, 8.95, 7.78, 7.28, 6.93, 6.62, 6.14, 5.53, 5.13, 4.77, 4.45, 4.14, 3.96, 3.79, 3.64, 3.52, 3.40, 3.28, 3.15, 3.05, 2.65, 2.63, 2.51 and 2.47 Å;

1.48 The free base crystal according to any of formulae 1.4-1.6, wherein said free base crystal exhibits an X-ray powder diffraction pattern comprising at least five peaks having d-spacing values selected from the group consisting of 12.51, 10.80, 5.53, 4.77, 4.45, 4.14, 3.96, 3.79, 3.64, 3.40, 3.28 and 3.15 Å;

1.49 The free base crystal according to any of formulae 1.4-1.6, wherein said free base crystal exhibits an X-ray powder diffraction pattern comprising at least five peaks having 2-theta angle and/or d-spacing values selected from those set forth in Table 6 below:

TABLE 6

| No | Pos. [°2Th.] | d-spacing [Å] | Height [cps] | Rel. Int. [%] |
|---|---|---|---|---|
| 1 | 7.06 | 12.5104 | 5115 | 36 |
| 2 | 8.18 | 10.7998 | 6755 | 48 |
| 3 | 9.88 | 8.9451 | 2095 | 15 |
| 4 | 11.36 | 7.7828 | 3285 | 24 |
| 5 | 12.14 | 7.2844 | 2975 | 21 |
| 6 | 12.76 | 6.9318 | 2960 | 21 |
| 7 | 13.36 | 6.6219 | 2305 | 17 |
| 8 | 14.42 | 6.1374 | 2580 | 19 |
| 9 | 16.00 | 5.5347 | 14250 | 100 |
| 10 | 17.26 | 5.1334 | 3785 | 27 |
| 11 | 18.60 | 4.7665 | 7430 | 53 |
| 12 | 19.92 | 4.4535 | 12475 | 88 |
| 13 | 21.42 | 4.1449 | 6725 | 48 |
| 14 | 22.42 | 3.9622 | 12260 | 87 |
| 15 | 23.44 | 3.7921 | 6950 | 49 |
| 16 | 24.44 | 3.6391 | 4010 | 29 |
| 17 | 25.28 | 3.5201 | 3780 | 27 |
| 18 | 26.20 | 3.3985 | 4255 | 30 |
| 19 | 27.14 | 3.2829 | 4995 | 36 |
| 20 | 28.28 | 3.1531 | 4805 | 34 |
| 21 | 29.22 | 3.0538 | 2995 | 22 |
| 22 | 33.80 | 2.6497 | 2510 | 18 |
| 23 | 34.04 | 2.6316 | 2515 | 18 |
| 24 | 35.78 | 2.5075 | 2310 | 17 |
| 25 | 36.28 | 2.4741 | 2075 | 15 | wherein the XRPD pattern is measured in a diffractometer using copper anode, e.g., at wavelength alpha1 of 1.5406 Å and wavelength alpha2 of 1.5444 Å;

1.50 The free base crystal according to any of formulae 1.4-1.6, wherein said free base crystal exhibits an X-ray powder diffraction pattern comprising at least five peaks having 2-theta angle and/or d-spacing values selected from those set forth in Table 6-A below:

TABLE 6-A

| Pos. [°2Th.] | d-spacing [Å] | Height [cps] | Rel. Int. [%] |
|---|---|---|---|
| 7.06 | 12.5104 | 5115 | 36 |
| 8.18 | 10.7998 | 6755 | 48 |
| 16.00 | 5.5347 | 14250 | 100 |
| 18.60 | 4.7665 | 7430 | 53 |
| 19.92 | 4.4535 | 12475 | 88 |
| 21.42 | 4.1449 | 6725 | 48 |
| 22.42 | 3.9622 | 12260 | 87 |
| 23.44 | 3.7921 | 6950 | 49 |
| 24.44 | 3.6391 | 4010 | 29 |
| 26.20 | 3.3985 | 4255 | 30 |
| 27.14 | 3.2829 | 4995 | 36 |
| 28.28 | 3.1531 | 4805 | 34 | wherein the XRPD pattern is measured in a diffractometer using copper anode, e.g., at wavelength alpha1 of 1.5406 Å and wavelength alpha2 of 1.5444 Å;

1.51 The free base crystal according to any of formulae 1.4-1.6 or 1.46-1.50, wherein said free base crystal exhibits an X-ray powder diffraction pattern corresponding with or substantially as depicted in FIG. 7-B;

1.52 The free base crystal according to any of formulae 1.4-1.6 or 1.46-1.51, wherein said free base crystal exhibits a Differential Scanning calorimetry (DSC) pattern comprising an endothermic peak at about 79° C., for example about 78.6° C.; or a Differential Scanning calorimetry (DSC) pattern corresponding with or substantially as depicted in FIG. 7-A;

1.53 The free base crystal according to any of the above formulae, wherein said free base crystal is in a single crystal form and are free or substantially free of any other form, e.g., less than 10 wt. %, preferably less than about 5 wt. %, more preferably less than about 2 wt. %, still preferably less than about 1 wt. %, still preferably less than about 0.1%, most preferably less than about 0.01 wt. % of amorphous form;

1.54 The free base crystal according to any of the above formulae, wherein said free base crystal is in a single crystal form and are free or substantially free of any other form, e.g., less than 10 wt. %, preferably less than about 5 wt. %, more preferably less than about 2 wt. %, still preferably less than about 1 wt. %, still preferably less than about 0.1%, most preferably less than about 0.01 wt. % of other crystal forms;

1.55 The free base crystal according to any of the above formulae, wherein said free base crystal is in a single crystal form and are free or substantially free of any other form, e.g., less than 10 wt. %, preferably less than about 5 wt. %, more preferably less than about 2 wt. %, still preferably less than about 1 wt. %, still preferably less than about 0.1%, most preferably less than about 0.01 wt. % of amorphous and other crystal forms;

1.56 The free base crystal according to any of the above formulae, wherein said free base crystal is made by any of processes described or similarly described below in Process III or in any of Examples 1-7 or Example 13.

In the second aspect, the invention provides a process (Process I) for the preparation of a salt of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]-pyrazolo[4,3-e]pyrimidin-4(2H)-one (Compound A), comprising:

(1) dissolving a crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base (Compound A), i.e., free base crystal of Compound A, in a non-solvate or solvate form in a solvent;

(2) adding an acid optionally in a solvent to the solution obtained in the step (1), and (3) stirring the mixture obtained in the step (2) to result in the objective salt.

In a further embodiment of the second aspect, the invention provides Process I, wherein the salt is a salt crystal, e.g., a fumarate (e.g., hemi-fumarate), phosphate (e.g., mono-phosphate), (1-hydrox-2)-naphthoate or mesylate salt crystal. Therefore, in a particular embodiment, useful acid of step (2) of Process I for making salt crystals of Compound A include fumaric acid, phosphoric acid, tartaric acid (e.g., L-tartaric acid) and methanesulfonic acid. The solvent useful for Process I to make salt crystals is methanol, acetonitrile, acetone or mixtures thereof. In another further embodiment, the salt is a benzoate salt crystal and useful acid of step (2) of Process I for making said benzoate salt crystal of Compound A is benzoic acid. The solvent useful for Process I to make the benzoate salt crystals includes ethyl acetate and xylene.

In a further embodiment of the second aspect, the invention provides a process (Process II) for the preparation of a mono-phosphate salt crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]-pyrazolo[4,3-e]pyrimidin-4(2H)-one (mono-phosphate salt crystal of Compound A), comprising:

(1) dissolving a crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base (i.e., free base crystal of Compound A) in a non-solvate or solvate form in a solvent;

(2) adding phosphoric acid in a solvent to the solution obtained in the step (1), and (3) stirring the mixture obtained in the step (2) to result in the objective mono-phosphate salt crystal.

In a further embodiment, the invention provides Process II for the preparation of a mono-phosphate salt crystal of Compound A as follows:

2.1 Process II as hereinbefore described, wherein the solvent in the step (1) is selected from acetone and acetonitrile;

2.2 Process II as hereinbefore described or 2.1, wherein the solvent in the step (2) is selected from acetone or acetonitrile;

2.3 Process II as hereinbefore described or 2.1 or 2.2, wherein the amount of phosphoric acid to be added in the step (2) is almost (about) equimolecular quantity to the amount of crystal of the (6aR,9aS)-5,6a,7,8,9,9a-hexahydro-5-methyl-3-(phenylamino)-2-((4-(6-fluoro-pyridin-2-yl)phenyl)methyl)-cyclopent[4,5]imidazo[1,2-a]pyrazolo[4,3-e]pyrimidin-4(2H)-one free base (free base crystal of Compound A) in non-solvate form or in solvate form of the step (1); In a particular embodiment, the amount of phosphoric acid to be added in step (2) is 0.5 to 2.0 equivalent, more preferred 0.8 to 1.2 equivalent, and the most preferred, 0.9 to 1.1 equivalent of the amount of crystal of the (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base (free base crystal of Compound A) in non-solvate form or in solvate form of the step (1);

2.4 Process II as hereinbefore described or any of 2.1-2.3, wherein water is additionally added in the step (2);
2.5 Process II as hereinbefore described or any of 2.1-2.4, wherein the mixture is stirred at 20 to 70° C. in the step (3);
2.6 Process II as hereinbefore described or any of 2.1-2.4, wherein the mixture is stirred at about 50° C., about 32° C., about 38° C. or about 39° C.;
2.7 Process II as hereinbefore described or any of 2.1-2.6, wherein the free base crystal of Compound A in step 1 is in a non-solvate form;
2.8 Process II as hereinbefore described or any of 2.1-2.6, wherein the free base crystal of Compound A in step 1 is in a solvate form, e.g., in an alcohol solvate form, e.g., in an ethanol solvate form, e.g., in a mono-ethanol solvate form.

In the third aspect, the invention provides a process for the preparation of a free base crystal of the Compound A in a solvate form or non-solvate form according to any of formulae 1.1-1.56 (Process III). In one embodiment, the invention provides a process for preparation of a crystal of the Compound (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base (free base crystal of Compound A) in solvate form (Process III-A), which comprises:
(1) stirring (6aR,9aS)-3-chloro-2-(4-(6-fluoropyridin-2-yl)benzyl)-5-methyl-5,6a,7,8,9,9a-hexahydrocyclopenta[4,5]-imidazo[1,2-a]pyrazolo[4,3-e]pyrimidin-4(2H)-one in a solvent in the presence of a base, an aniline, a palladium catalyst and a ligand, then separating organic layer;
(2) adding the solvent corresponding to objective solvate form to the organic layer obtained in the step (1).

In another embodiment of the third aspect, the invention provides a process for the preparation of a crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base (free base crystal of Compound A) in non-solvate form (Process III-B), which comprises:
(1) stirring (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one in a solvent in the presence of a base, an aniline, a palladium catalyst and a ligand, then separating the organic layer;
(2) adding the seed crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base in non-solvate form to the organic layer obtained in the step (1).

Base useful for Process III of the invention as described hereinbefore includes but not limited to carbonate, bicarbonate, phosphate or hydroxide of an alkali or alkaline earth metal (e.g. sodium, magnesium, calcium, potassium, cesium or barium carbonate, bicarbonate, hydroxide, butoxide or phosphate, for example sodium carbonate, sodium bicarbonate, sodium hydroxide, sodium t-butoxide, calcium carbonate, potassium carbonate, potassium hydroxide, potassium t-butoxide, potassium phosphate, cesium carbonate, cesium hydroxide). Preferably, the base according to step (1) of the process of the invention is potassium carbonate or $K_2CO_3$. Preferably, the palladium catalyst useful in step (1) of Process III of the invention includes but is not limited to palladium II acetate, palladium chloride, palladium bromide, $Pd(PPh_3)_4$, $PdCl_2(PPh_3)_2$, Pd (dba)$_2$, Pd/C and tris(dibenzylideneacetone)dipalladium(0). Preferably, the palladium catalyst useful for Process III of the current invention is palladium II acetate or $Pd(OAc)_2$.

The ligand useful for Process III of the invention is a bidentate ligand, preferably xantphos.

Solvent useful for Process III of the invention includes organic solvent such as toluene, tetrahydrofuran, xylene, dimethylacetamide, preferable, xylene or combination of dimethylacetamide and xylene.

Process III of the invention is preferably carried out under nitrogen atmosphere. Between Step (1) and Step (2) of Process III of the invention, the separated organic layer is preferably washed with a suitable solution and then treated with charcoal to remove residual palladium catalyst. In one embodiment, step (1) of Process III as hereinbefore described further comprises the step of adding water, e.g., before separating the organic layer. In another embodiment, step (1) of Process III as hereinbefore described further comprises the step of adding a solution of cystein in water optionally with additional solvent (e.g., with additional dimethylacetamide and xylene).

In another embodiment of the third aspect, the invention provides Process III-C, wherein the crystal of the Compound A (i.e., free base crystal of Compound A) in solvate form is prepared by using the salt crystal of the Compound A. Therefore, the invention provides a process for making the crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base (free base crystal of Compound A) in solvate form, comprising:
(1) dissolving the salt crystal of (6aR,9aS)-5,6a,7,8,9,9a-hexahydro-5-methyl-3-(phenylamino)-2-((4-(6-fluoro-pyridin-2-yl)phenyl)methyl)-cyclopent[4,5]imidazo[1,2-a]pyrazolo[4,3-e]pyrimidin-4(2H)-one (Compound A), (i.e., the salt crystal of Compound A), in a non-solvate or solvate form, in mixture of an organic solvent, water and an aqueous base solution;
(2) separating the organic layer;
(3) adding a solvent to step (2) to form the objective solvate;
(4) stirring the mixture obtained in step (3) to result in the objective crystals.

The salt crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one (salt crystals of Compound A) may be a fumarate, for example, hemi-fumarate; phosphate (e.g., mono-phosphate); (1-hydro-2)-naphthoate; mesylate; or benzoate salt crystal. In a preferred embodiment, the free base crystal of Compound A being prepared is in an ethanol solvate form (e.g., mono-ethanol solvate form) and the salt crystal of step (1) is in an hemi-fumarate, ethyl acetate/acetone solvate form (e.g., hemi-fumarate, 0.5 ethyl acetate, 0.3 acetone solvate form).

The salt crystals of step (1) of Process III may be prepared by (1) stirring (6aR,9aS)-3-chloro-2-(4-(6-fluoropyridin-2-yl)benzyl)-5-methyl-5,6a,7,8,9,9a-hexahydrocyclopenta-[,5]imidazo[1,2-a]pyrazolo[4,3-e]pyrimidin-4(2H)-one (Compound A) in a solvent in the presence of a base, an aniline, a palladium catalyst and a ligand; (2) separating organic layer; (3) adding an acid optionally in a solvent to the solution obtained in the step (2), and stirring the mixture obtained in the step (3) to result in the objective salt. Useful base, palladium catalyst, ligand and solvent of step (1) are previously defined in Process III. Useful acid of step (2) are previously defined in Process I (e.g., fumaric acid, phosphoric acid, tartaric acid (e.g., L-tartaric acid), methanesulfonic acid as well as benzoic acid).

The free base crystal of Compound A prepared by Process III-C is also useful for the preparation of the salt crystal described in Process I, particularly the mono-phosphate salt crystal described in Process II. Therefore, in a particular embodiment, the invention provides a process for the preparation of the salt crystal of Compound A according to Process I hereinbefore described, further comprises the steps of preparing the free base crystal of Compound A according to Process III-C as hereinbefore described. Therefore, the invention provides a process for preparing the salt crystal of Compound A comprising (a) preparing the free base crystal of Compound A as described in process III-A, III-B or III-C; (b) isolating the free base crystal of Compound A from step (a); (c) dissolving the free base crystals prepared from Process III-A, III-B or III-C; (d) adding an acid optionally in a solvent to the solution obtained in step (c) and (e) stirring the mixture obtained in step (d) to result in the objective salt. In another particular embodiment, the invention provides a process for the preparation of a mono-phosphate salt crystal of Compound A comprising: (a) preparing the free base crystal of the Compound A as described in III-C; (b) isolating the free base crystal of Compound A from step (a); and (c) dissolving the free base crystals prepared from Process III-C; (d) adding an acid optionally in a solvent to the solution obtained in step (c) and (e) stirring the mixture obtained in step (d) to result in the objective salt. Therefore, in a particular embodiment, the invention provides a process for the preparation of a mono-phosphate salt crystal of Compound A comprising:

(a) dissolving the salt crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]-pyrimidin-4(2H)-one (compound A) in hemi-fumarate in a non-solvate or solvate form, in the mixture of an organic solvent and aqueous basic solution;
(b) separating the organic layer;
(c) adding ethanol, to the organic solution obtained in the step (b);
(d) stirring the mixture obtained in the step (c) to result in the objective crystal;
(e) isolating the crystals obtained form step (d);
(f) dissolving the crystals obtained from step (e);
(g) adding phosphoric acid (e.g., 0.5 to 2.0 equivalent, preferably 0.8 to 1.2 equivalent, more preferably, 0.9 to 1.1 equivalent of the amount of the free base crystal of Compound A) in a solvent to the solution obtained in step (f); and
(h) stirring the mixture obtained in step (g) to result in the objective salt.

In the fourth aspect, the invention provides a novel salt crystal of Compound A. Therefore, the invention provides salt crystal of Compound A in hemi-fumarate, 0.5 ethyl acetate, 0.3 acetone solvate form; or in benzoate non-solvate form.

The salt crystal of Compound A in hemi-fumarate, 0.5 ethyl acetate, 0.3 acetone solvate form, wherein the salt crystal exhibits an X-ray powder diffraction pattern comprising at least five peaks having d-spacing values selected from the group consisting of: 14.67, 11.97, 10.99, 8.19, 7.41, 6.98, 6.46, 6.14, 5.89, 5.59, 5.20, 5.01, 4.66, 4.61, 4.30, 4.07, 3.93, 3.74, 3.59, 3.47, 3.34, 3.23, 3.06, 3.00, 2.94, 2.86, 2.80, 2.62, 2.54, 2.51 and 2.40 Å. In a further embodiment, the salt crystal of Compound A in hemi-fumarate, 0.5 ethyl acetate, 0.3 acetone solvate form, wherein the salt crystal exhibits an X-ray powder diffraction pattern comprising at least five peaks having d-spacing values selected from the group consisting of: 14.67, 11.97, 7.41, 6.98, 6.46, 5.20, 5.01, 4.66, 4.30, 4.07, 3.93, 3.74 and 3.59 Å. In another embodiment, the hemi-fumarate, 0.5 ethyl acetate, 0.3 acetone solvate salt crystal of the invention as hereinbefore described exhibits an X-ray powder diffraction pattern substantially as depicted in FIG. 8-B. In still another embodiment, hemi-fumarate, 0.5 ethyl acetate, 0.3 acetone solvate salt crystal of the invention exhibits a differential scanning calorimetry pattern substantially as depicted in FIG. 8-A.

The salt crystal of Compound A in benzoate non-solvate form, wherein the salt crystal exhibits an X-ray powder diffraction pattern comprising at least five peaks having d-spacing values selected from the group consisting of: 14.15, 12.17, 7.31, 5.93, 5.59, 5.15, 4.52, 4.07, 3.92, 3.64, 3.50, 3.42, 3.29, 3.21 and 3.11 Å. In a further embodiment, the salt crystal of Compound A in benzoate non-solvate form exhibits an X-ray powder diffraction pattern comprising all of the peaks having d-spacing values selected from the group consisting of: 14.15, 7.31, 5.15, 4.07 and 3.92 Å. In another embodiment, the benzoate non-solvate salt crystal of the invention as hereinbefore described exhibits an X-ray powder diffraction pattern substantially as depicted in FIG. 9-B. In still another embodiment, benzoate non-solvate salt crystal of the invention exhibits a differential scanning calorimetry pattern substantially as depicted in FIG. 9-A.

In the fifth aspect, the invention provides a pharmaceutical composition comprising the monophosphate salt crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one (Compound A) in admixture with a pharmaceutically acceptable diluent or carrier. In a particular embodiment, the pharmaceutically acceptable diluents or carrier is selected from the group mannitol, microcrystalline cellulose, hydorxypropyl cellulose, sodium starch glycolate, magnesium stearate, hypromellose, polyethylene glycol, titanium dioxide, ferric oxide (red and/or yellow). In another particular embodiment, the pharmaceutical composition of the invention comprises the following:

| Components | Quantity per Tablet (mg) |
|---|---|
| Compound A monophosphate salt crystal | 35.79 |
| (as the free base equivalent) | (30) |
| Mannitol | 85.01 |
| Microcrystalline Cellulose | 15.0 |
| Hydroxypropyl Cellulose | 4.5 |
| Sodium Starch Glycolate | 7.5 |
| Magnesium Stearate | 2.2 |
| Hypromellose 2910 | 4.5 |
| Polyethylene Glycol 8000 | 1.0 |
| Titanium Dioxide | 0.5 |
| Ferric Oxide, Red | 0.05 |
| Ferric Oxide, Yellow | 0.05 |
| TOTAL | 156.1 |

BRIEF DESCRIPTION OF THE DRAWINGS

FIG. 1-A depicts a Differential Scanning calorimetry (DSC) thermograph of the mono-ethanol solvate crystals of (6aR,9aS)-3-chloro-2-(4-(6-fluoropyridin-2-yl)benzyl)-5- methyl-5,6a,7,8,9,9a-hexahydrocyclopenta-[4,5]imidazo[1,2-a]pyrazolo[4,3-e]pyrimidin-4(2H)-one free base (Compound A).

FIG. 1-B depicts an X-ray Powder Diffraction pattern of the mono-ethanol solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one free base (Compound A).

FIG. 2-A depicts a Differential Scanning calorimetry (DSC) thermograph of the mono-n-propanol solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one free base (Compound A).

FIG. 2-B depicts an X-ray Powder Diffraction pattern of the mono-n-propanol solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one free base (Compound A).

FIG. 3-A depicts a Differential Scanning calorimetry (DSC) thermograph of the mono-2-propanol solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one free base (Compound A).

FIG. 3-B depicts an X-ray Powder Diffraction pattern of the mono-2-propanol solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one free base (Compound A).

FIG. 4-A depicts a Differential Scanning calorimetry (DSC) thermograph of the non-solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one free base (Compound A).

FIG. 4-B depicts an X-ray Powder Diffraction pattern of the non-solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one free base (Compound A).

FIG. 5-A depicts a Differential Scanning calorimetry (DSC) thermograph of the mono-methanol solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one free base (Compound A).

FIG. 5-B depicts an X-ray Powder Diffraction pattern of the mono-methanol solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one free base (Compound A).

FIG. 6-A depicts an X-ray Powder Diffraction pattern of the mono-ethanol solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one free base (Compound A).

FIG. 6-B depicts a Differential Scanning calorimetry (DSC) thermograph and thermogravimetric analysis (TGA) of the mono-ethanol solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one free base (Compound A).

FIG. 7-A depicts a Differential Scanning calorimetry (DSC) thermograph of the mono-n-butanol solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one free base (Compound A).

FIG. 7-B depicts an X-ray Powder Diffraction pattern of the mono-n-butanol solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one free base (Compound A).

FIG. 8-A depicts a Differential Scanning calorimetry (DSC) thermograph of the hemi-fumarate 0.5 ethyl acetate 0.3 acetone solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one (Compound A).

FIG. 8-B depicts an X-ray Powder Diffraction pattern of the hemi-fumarate 0.5 ethyl acetate 0.3 acetone solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one (Compound A).

FIG. 9-A depicts a Differential Scanning calorimetry (DSC) thermograph of the benzoate non-solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one (Compound A).

FIG. 9-B depicts an X-ray Powder Diffraction pattern of the benzoate non-solvate crystals of (6aR,9aS)-3-chloro-2-(4-(6-fluoropyridin-2-yl)benzyl)-5-methyl-5,6a,7,8,9,9a-hexahydrocyclopenta-[4,5]imidazo[1,2-a]pyrazolo[4,3-e]pyrimidin-4(2H)-one (Compound A).

DETAIL DESCRIPTION

As use herein, the term "crystal" or "crystals" or "crystalline" or "crystalinic" refers to any solid that has a short or long range order of the molecules, atoms or ions in a fixed lattice arrangement. Crystals of the present invention may be in a single crystal form. Therefore, the crystals of the present invention may be in a triclinic, monoclinic, orthorhombic, tetragonal, rhobohedral, hexagonal or cubic crystal form or mixtures thereof. In particular embodiment, the crystals of the present invention are in dry crystalline form. In another particular embodiment, the crystals of the present invention are substantially free of other forms, e.g., free of amorphous or other crystal forms.

The term "substantially free" of other crystal forms refers to less than about 10 wt. %, preferably less than about 5 wt. %, more preferably less than about 2 wt. %, still preferably less than about 1 wt. %, still preferably less than about 0.1%, most preferably less than about 0.01 wt. % of other crystal forms, e.g., amorphous or other crystal forms.

The term "predominantly" or "substantially entirely in a single form" refers to less than about 10 wt. %, preferably less than about 5 wt. %, more preferably less than about 2 wt. %, still preferably less than about 1 wt. %, still preferably less than about 0.1%, most preferably less than about 0.01 wt. % of other crystal forms, e.g., amorphous or other crystal forms.

In particular embodiment, the Crystals of the invention may be contain an amount of solvent, e.g., in solvate form, or trace amounts of water, e.g., in hydrate form. Preferably, the Crystals of the invention are in solvate form or non-solvate form. Still preferably, the crystals of the invention are in solvate and non-hydrate form.

The mono-phosphate salt crystals of the invention preferably have a free base to acid ratio of 1 to 1. For example, the phosphate salt crystal of the invention may comprise 1 molar equivalent of the free base to 1 molar equivalent of phosphate.

The term "solvate" refers to crystalline solid adducts containing either stoichiometric or nonstoichiometric amounts of a solvent incorporated within the crystal structure. Therefore, the term "non-solvate" form herein refers to crystals that are free or substantially free of solvent molecules within the crystal structures of the invention. Similarly, the term "non-hydrate" form herein refers to crystals that are free or substantially free of water molecules within the crystal structures of the invention.

The term "amorphous" form refers to solids of disordered arrangements of molecules and do not possess a distinguishable crystal lattice.

Unless further modified, the term "Compound A" refers to (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in free base form, having the following structure:

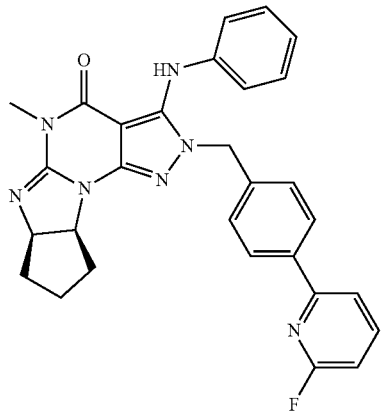 [SMILES: CN1C(=O)c2c(nn(Cc3ccc(-c4cccc(F)n4)cc3)c2Nc2ccccc2)N2C1=N[C@@H]1CCC[C@@H]12]

The phrase "crystal of Compound A" refers to the crystal of the compound A in free base form. The term "free base crystal" is also used to refer to such crystal. Therefore, "free base crystal of Compound A" also refers to the crystal of Compound A in free base form. The term "salt crystal" is intended to refer to the crystal of Compound A in salt form.

The crystallinity or the morphology of the crystals of the present Invention may be determined by a number of methods, including, but not limited to single crystal X-ray diffraction, X-ray powder diffraction, polarizing optical microscopy, thermal microscopy, differential scanning calorimetry (DSC), thermogravimetric analysis (TGA), infared adsorption spectroscopy and Raman spectroscopy. Characterization of solvates or hydrates or lack thereof may also be determined by DSC and/or TGA.

It is to be understood that X-ray powder diffraction and the differential scanning calorimetry pattern of a given sample may vary a little depending on the instrument used, the time and temperature of the sample when measured and standard experimental errors. Therefore, the temperature and the 2-theta values, d-spacing values, heights and relative intensity of the peaks as setforth herein in Tables 1-6 or in FIGS. 1-A to 9-A and 1-B to 9B will have an acceptable level of deviation. For example, the values may have an acceptable deviation of e.g., about 20%, 15%, 10%, 5%, 3%, 2% or 1%. In one embodiment, the 2-theta values and/or d-spacing values of the XRPD pattern of the crystals of the current invention have an acceptable deviation of ±0.2 degrees and/or Å. Further, the XRPD pattern of the crystals of the invention may be identified by the characteristic peaks as recognized by one skilled in the art. For example, the crystals of the invention may be identified by e.g., at least five characteristic peaks, e.g., at least three or at least five peaks, e.g., at least three or at least five peaks having 2-theta values and/or at least three or at least five peaks having d-spacing values as setforth in the XRPD patterns setforth herein. In another embodiment, the crystals of the invention may be identified by 2-theta values and/or d-spacing values as setforth in the XRPD patterns provided herein. Therefore, the term "corresponding with or substantially as" set forth in any of Tables 1-6 or depicted in any of FIG. 1-B, 2-B, 3-B, 4-B, 5-B, 6-A, 7-B, 8-B or 9-B refers to any crystals which have an XRPD pattern comprising the major or characteristic peaks as set forth in the tables/figures.

The term "about" in front of a numerical value refers to the numerical value itself or the numerical value itself ±20%, ±15%, ±10%, preferably ±5%, preferably ±3%, preferably ±2%, preferably ±1% of that value. For example, when referencing temperature, the term "about" refers to the temperature itself ±10° C., preferably ±5° C., preferably ±3° C. of the reference temperature. In another example, when referencing 2-theta angle values, the term "about" refers to the numerical 2-theta angle value itself ±0.2 degrees of the reference 2-theta angle value. In still another example, when referencing d-spacing values, the term "about" refers to the numerical 2-theta angle value itself ±0.2 Å of the reference d-spacing value.

EXAMPLES

The method of making the Compound (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one is generally described in WO 2009/075784, the contents of which are incorporated by reference in their entirety. This compound can also be prepared as summarized or similarly summarized in the following reaction scheme.

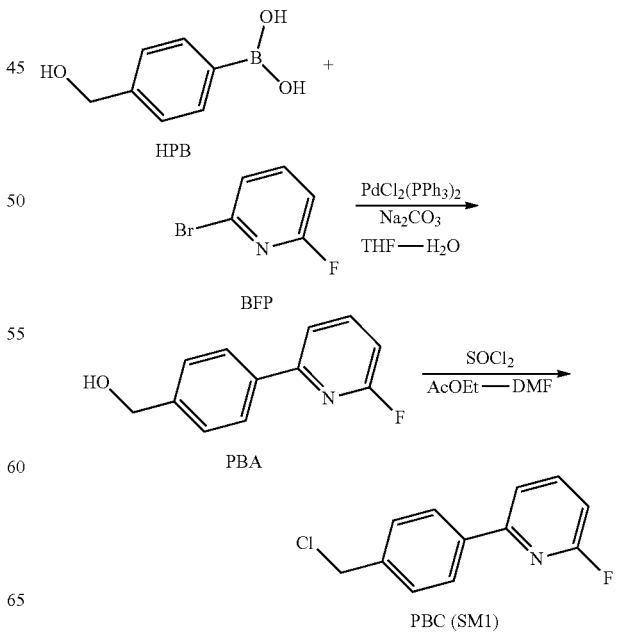

21
-continued
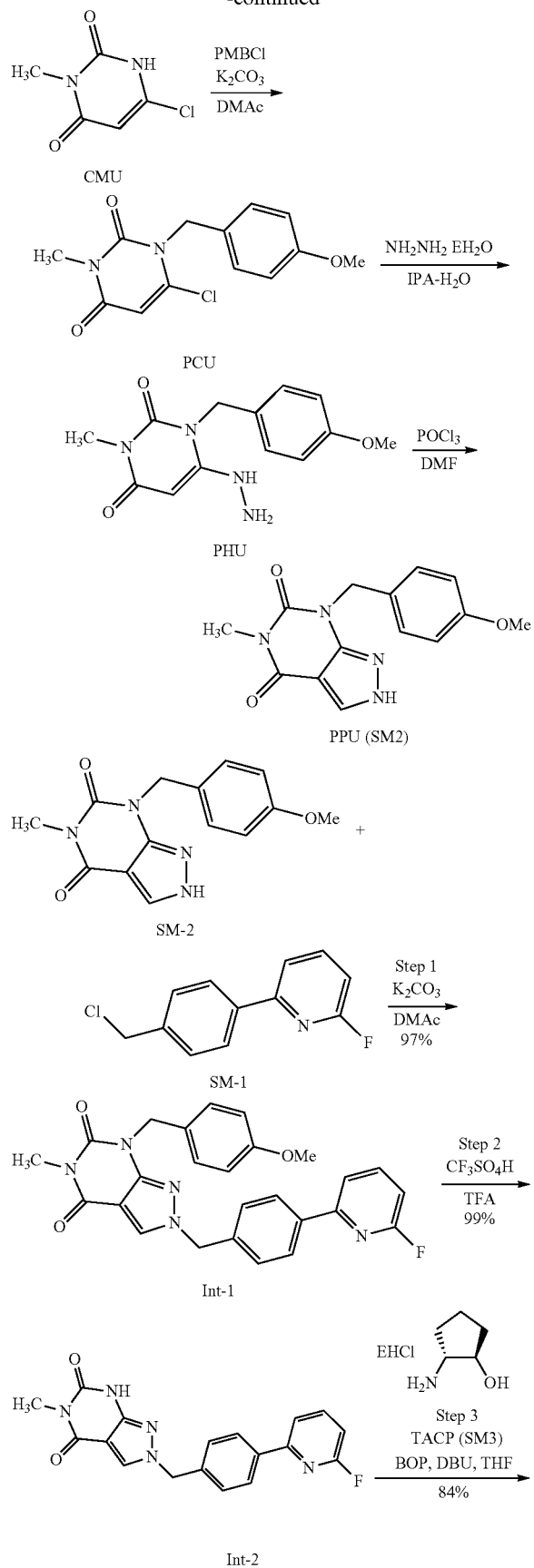
22
-continued
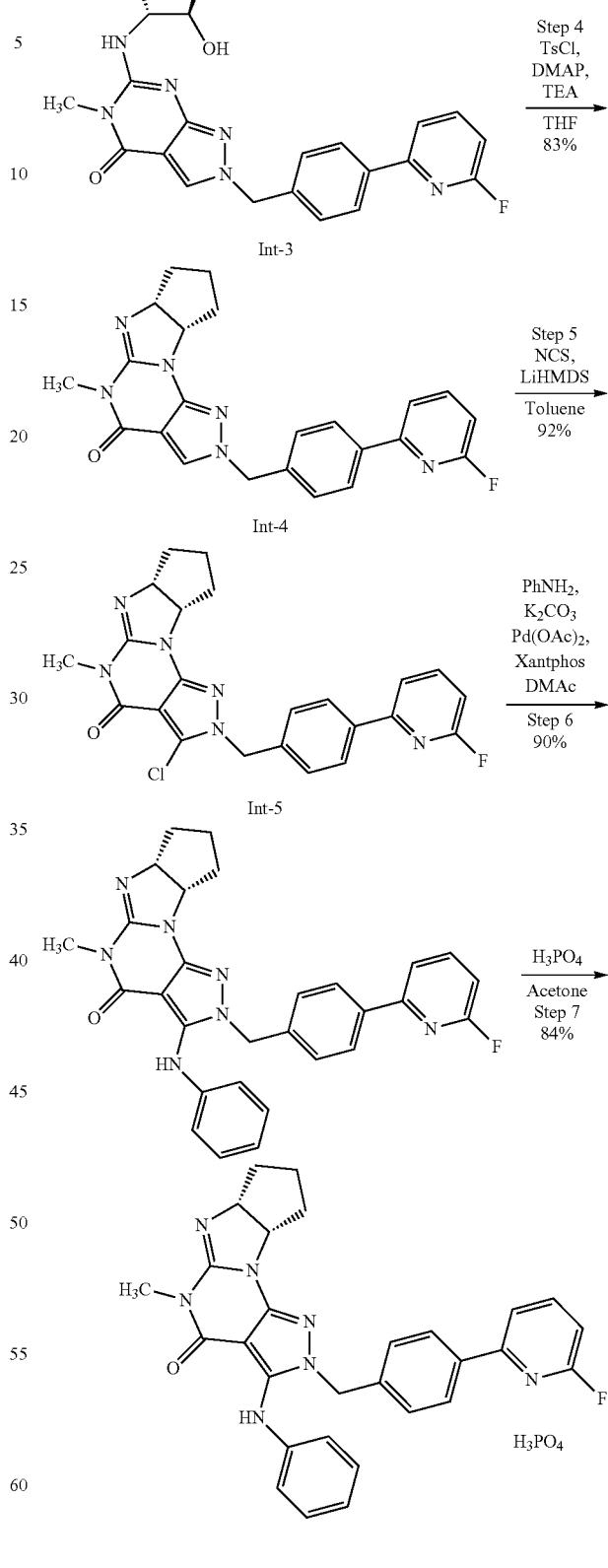
In particular, (6aR,9aS)-3-chloro-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one (Int-5) may be prepared as described or similarly described below. The free base crystals and the mono-phosphate salt crystals of the invention may be prepared by using the methods described or similarly described in Examples 1-14 below.

Preparation of (6aR,9aS)-3-chloro-2-(4-(6-fluoro-pyridin-2-yl)benzyl)-5-methyl-5,6a,7,8,9,9a-hexahydrocyclopenta[4,5]imidazo[1,2-a]pyrazolo[4,3-e]pyrimidin-4(2H)-one (4-(6-fluoropyridin-2-yl)phenyl)methanol

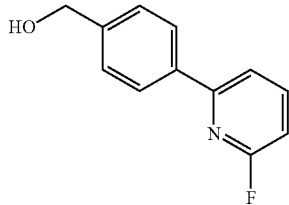 [SMILES: OCc1ccc(-c2cccc(F)n2)cc1]

The mixture of Na$_2$CO$_3$ (121 g), water (500 mL), THF (650 mL), PdCl$_2$(PPh$_3$)$_2$ (997 mg), 2-bromo-6-fluoropyridine (100 g) and 4-(hydroxymethyl)phenylboronic acid (90.7 g) is stirred at 65° C. for 4 h under the nitrogen atmosphere. After cooling to room temperature, THF (200 mL) is added. The organic layer is separated and washed with 5% NaCl solution twice. The organic layer is concentrated to 400 mL. After the addition of toluene (100 mL), heptane (500 mL) is added at 55° C. The mixture is cooled to room temperature. The crystals are isolated by filtration, washed with the mixture of toluene (100 mL) and heptane (100 mL) and dried to give (4-(6-fluoropyridin-2-yl)phenyl)methanol (103 g). $^1$H NMR (500 MHz, CDCl$_3$) δ 1.71-1.78 (m, 1H), 4.74-4.79 (m, 2H), 6.84-6.88 (m, 1H), 7.44-7.50 (m, 2H), 7.61-7.65 (m, 1H), 7.80-7.88 (m, 1H), 7.98-8.04 (m, 2H).

2-(4-(chloromethyl)phenyl)-6-fluoropyridine

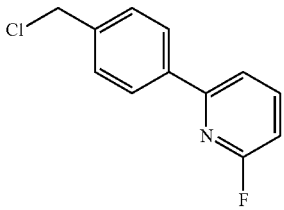 [SMILES: Fc1cccc(-c2ccc(CCl)cc2)n1]

The solution of thionylchloride (43.1 mL) in AcOEt (200 mL) is added to the mixture of (4-(6-fluoropyridin-2-yl)phenyl)methanol (100 g), DMF (10 mL) and AcOEt (600 mL) at room temperature. The mixture is stirred at room temperature for 1 h. After cooling to 10° C., 15% Na$_2$CO$_3$ solution is added. The organic layer is separated and washed with water (500 mL) and 5% NaCl solution (500 mL) twice. The organic layer is concentrated to 500 mL. After the addition of EtOH (500 mL), the mixture is concentrated to 500 mL. After addition of EtOH (500 mL), the mixture is concentrated to 500 mL. After the addition of EtOH (500 mL), the mixture is concentrated to 500 mL. After addition of EtOH (200 mL), water (700 mL) is added at 40° C. The mixture is stirred at room temperature. The crystals are isolated by filtration and dried to give 2-(4-(chloromethyl)phenyl)-6-fluoropyridine (89.5 g). $^1$H NMR (500 MHz, CDCl$_3$) δ 4.64 (s, 2H), 6.86-6.90 (m, 1H), 7.47-7.52 (m, 2H), 7.60-7.65 (m, 1H), 7.82-7.88 (m, 1H), 7.98-8.03 (m, 2H).

6-chloro-1-(4-methoxybenzyl)-3-methylpyrimidine-2,4(1H,3H)-dione

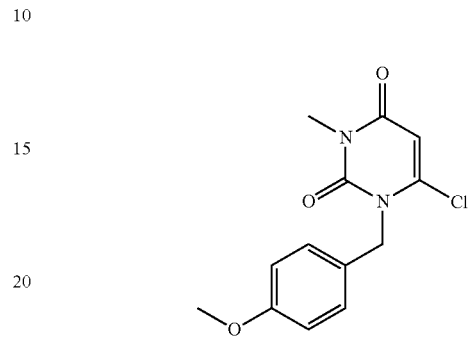

The mixture of 6-chloro-3-methyluracil (100 g), p-methoxybenzylchloride (107 g), K$_2$CO$_3$ (86.1 g) and DMAc (600 mL) is stirred at 75° C. for 4 h. Water (400 mL) is added at 45° C. and the mixture is cooled to room temperature. Water (800 mL) is added and the mixture is stirred at room temperature. The crystals are isolated by filtration, washed with the mixture of DMAc and water (1:2, 200 mL) and dried to give 6-chloro-1-(4-methoxybenzyl)-3-methylpyrimidine-2,4(1H,3H)-dione (167 g). $^1$H NMR (500 MHz, CDCl$_3$) δ 3.35 (s, 3H), 3.80 (s, 3H), 5.21 (s, 2H), 5.93 (s, 1H), 6.85-6.89 (m, 2H), 7.26-7.32 (m, 2H).

6-hydrazinyl-1-(4-methoxybenzyl)-3-methylpyrimidine-2,4(1H,3H)-dione

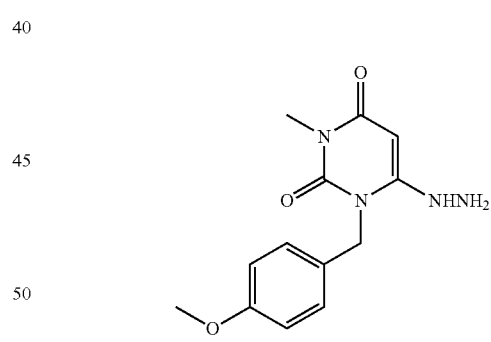

The mixture of 6-chloro-1-(4-methoxybenzyl)-3-methylpyrimidine-2,4(1H,3H)-dione (165 g), IPA (990 mL), water (124 mL) and hydrazine hydrate (62.9 mL) is stirred at room temperature for 1 h. The mixture is warmed to 60° C. and stirred at the same temperature for 4 h. Isopropyl acetate (1485 mL) is added at 45° C. and the mixture is stirred at the same temperature for 0.5 h. The mixture is cooled at 10° C. and stirred for 1 h. The crystals are isolated by filtration, washed with the mixture of IPA and isopropyl acetate (1:2, 330 mL) and dried to give 6-hydrazinyl-1-(4-methoxybenzyl)-3-methylpyrimidine-2,4(1H,3H)-dione (153 g). $^1$H NMR (500 MHz, DMSO-d$_6$) δ 3.12 (s, 3H), 3.71 (s, 3H), 4.36 (s, 2H), 5.01 (s, 2H), 5.14 (s, 1H), 6.87-6.89 (m, 2H), 7.12-7.17 (m, 2H), 8.04 (s, 1H).

7-(4-methoxybenzyl)-5-methyl-2H-pyrazolo[3,4-d]pyrimidine-4,6(5H,7H)-dione

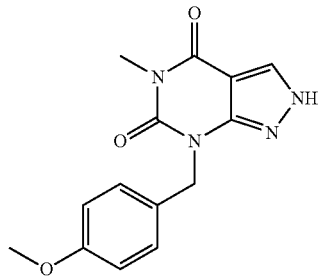 [SMILES: COc1ccc(Cn2c(=O)n(C)c(=O)c3c[nH]nc32)cc1]

To the mixture of DMF (725 mL) and 6-hydrazinyl-1-(4-methoxybenzyl)-3-methylpyrimidine-2,4(1H,3H)-dione (145 g) is added POCl$_3$ (58.5 mL) at 5° C. The mixture is stirred at room temperature for 1 h. Water (725 mL) is added at 50° C. and the mixture is stirred at room temperature for 1 h. The crystals are isolated by filtration, washed with the mixture of DMF and water (1:1, 290 mL) and dried to give 7-(4-methoxybenzyl)-5-methyl-2H-pyrazolo[3,4-d]pyrimidine-4,6(5H,7H)-dione (145 g). $^1$H NMR (500 MHz, DMSO-d$_6$) δ 3.23 (s, 3H), 3.71 (s, 3H), 5.05 (s, 2H), 6.82-6.90 (m, 2H), 7.28-7.36 (m, 2H), 8.48 (s, 1H), 13.51 (br, 1H).

2-(4-(6-fluoropyridin-2-yl)benzyl)-7-(4-methoxybenzyl)-5-methyl-2H-pyrazolo[3,4-d]pyrimidine-4,6(5H,7H)-dione

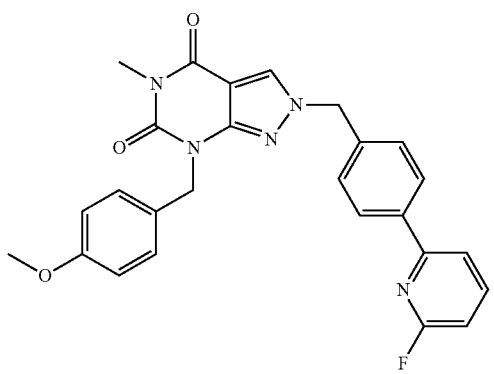 [SMILES: COc1ccc(Cn2c(=O)n(C)c(=O)c3cn(Cc4ccc(-c5cccc(F)n5)cc4)nc32)cc1]

The mixture of 2-(4-(chloromethyl)phenyl)-6-fluoropyridine (100 g), 7-(4-methoxybenzyl)-5-methyl-2H-pyrazolo[3,4-d]pyrimidine-4,6(5H,7H)-dione (129 g), K$_2$CO$_3$ (62.3 g) and DMAc (1500 mL) is stirred at 45° C. for 5 h. Water (1500 mL) is added at 40° C. and the mixture is stirred at room temperature for 1 h. The crystals are isolated by filtration, washed with the mixture of DMAc and water (1:1, 500 mL) and dried to give 2-(4-(6-fluoropyridin-2-yl)benzyl)-7-(4-methoxybenzyl)-5-methyl-2H-pyrazolo[3,4-d]pyrimidine-4,6(5H,7H)-dione (207 g). $^1$H NMR (500 MHz, DMSO-d$_6$) δ 3.21 (s, 3H), 3.66 (s, 3H), 4.98 (s, 2H), 5.45 (s, 2H), 6.77-6.82 (m, 2H), 7.13-7.16 (m, 1H), 7.25-7.30 (m, 2H), 7.41-7.44 (m, 2H), 7.92-7.96 (m, 1H), 8.04-8.11 (m, 3H), 8.68 (s, 1H).

2-(4-(6-fluoropyridin-2-yl)benzyl)-5-methyl-2H-pyrazolo[3,4-d]pyrimidine-4,6(5H,7H)-dione

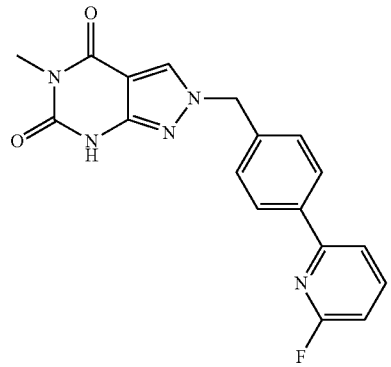 [SMILES: Cn1c(=O)[nH]c2nn(Cc3ccc(-c4cccc(F)n4)cc3)cc2c1=O]

The mixture of 2-(4-(6-fluoropyridin-2-yl)benzyl)-7-(4-methoxybenzyl)-5-methyl-2H-pyrazolo[3,4-d]pyrimidine-4,6(5H,7H)-dione (105 g), CF$_3$COOH (300 mL) and CF$_3$SO$_3$H (100 g) is stirred at room temperature for 10 h. Acetonitrile (1000 mL) is added. The mixture is added to the mixture of 25% NH$_3$ (1000 mL) and acetonitrile (500 mL) at 10° C. The mixture is stirred at room temperature for 1 h. The crystals are isolated by filtration, washed with the mixture of acetonitirile and water (1:1, 500 mL) and dried to give the crude product. The mixture of the crude product and AcOEt (1200 mL) is stirred at room temperature for 1 h. The crystals are isolated by filtration, washed with AcOEt (250 mL) and dried to give 2-(4-(6-fluoropyridin-2-yl)benzyl)-5-methyl-2H-pyrazolo[3,4-d]pyrimidine-4,6(5H,7H)-dione (75.3 g). $^1$H NMR (500 MHz, DMSO-d$_6$) δ 3.16 (s, 3H), 3.50-4.00 (br, 1H), 5.40 (s, 2H), 7.13-7.16 (m, 1H), 7.41-7.44 (m, 2H), 7.91-7.94 (m, 1H), 8.04-8.10 (m, 3H), 8.60 (s, 1H).

2-(4-(6-fluoropyridin-2-yl)benzyl)-6-(((1R,2R)-2-hydroxycyclopentyl)amino)-5-methyl-2H-pyrazolo[3,4-d]pyrimidin-4(5H)-one

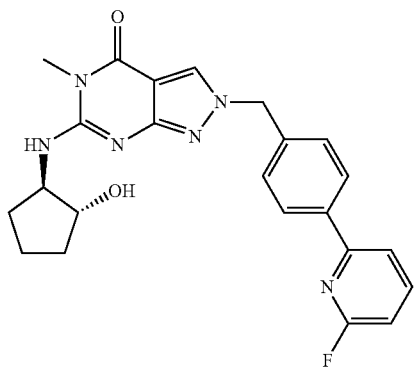 [SMILES: Cn1c(N[C@@H]2CCC[C@H]2O)nc2nn(Cc3ccc(-c4cccc(F)n4)cc3)cc2c1=O]

The mixture of BOP reagent (126 g), 2-(4-(6-fluoropyridin-2-yl)benzyl)-5-methyl-2H-pyrazolo[3,4-d]pyrimidine-4,6(5H,7H)-dione (80 g), DBU (136 mL) and THF (1120 mL) is stirred at room temperature for 1 h. (1R,2R)-2-Aminocyclopentanol hydrochloride (37.6 g) and THF (80 mL) are added and the mixture is stirred at room temperature for 5 h. After the addition of 5% NaCl (400 mL) and AcOEt (800 mL), the organic layer is separated. The organic layer is washed with 10% NaCl (400 mL), 1M HCl 15% NaCl (400 mL), 5% NaCl (400 mL), 5% NaHCO$_3$ (400 mL) and 5% NaCl (400 mL) successively. After treatment with active charcoal, the organic layer is concentrated to 400 mL. After the addition of acetonitrile (800 mL), the mixture is concentrated to 400 mL. After the addition of acetonitrile (800 mL), seed crystals are added at 40° C. The mixture is concentrated to 400 mL. Water (800 mL) is added at room temperature and the mixture is stirred for 2 h. The crystals are isolated by filtration, washed with the mixture of acetonitrile and water (1:2, 400 mL) and dried to give 2-(4-(6-fluoropyridin-2-yl)benzyl)-6-(((1R,2R)-2-hydroxycyclopentyl)amino)-5-methyl-2H-pyrazolo[3,4-d]pyrimidin-4(5H)-one (81.7 g). $^1$H NMR (500 MHz, CDCl$_3$) δ 1.47-1.59 (m, 1H), 1.68-1.93 (m, 3H), 2.02-2.12 (m, 1H), 2.24-2.34 (m, 1H), 3.42 (s, 3H), 3.98-4.12 (m, 2H), 4.68-4.70 (m, 1H), 5.37 (s, 2H), 6.86-6.90 (m, 1H), 7.36-7.42 (m, 2H), 7.58-7.63 (m, 1H), 7.81-7.88 (m, 1H), 7.89 (s, 1H), 7.97-8.01 (m, 2H).

(6aR,9aS)-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one

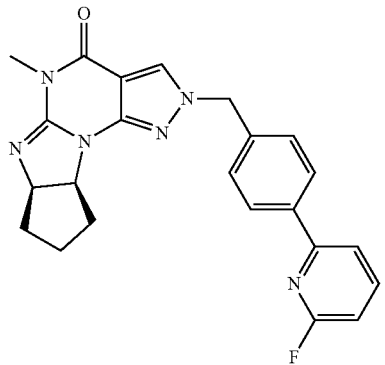 [SMILES: CN1C(=O)c2cn(Cc3ccc(-c4cccc(F)n4)cc3)nc2N2C1=N[C@@H]1CCC[C@@H]12]

The mixture of 2-(4-(6-fluoropyridin-2-yl)benzyl)-6-(((1R,2R)-2-hydroxycyclopentyl)amino)-5-methyl-2H-pyrazolo[3,4-d]pyrimidin-4(5H)-one (80 g), p-toluenesulfonylchloride (38.6 g), Et$_3$N (28.2 mL), N,N-dimethylaminopyridine (24.7 g) and THF (800 mL) is stirred at 50° C. for 10 h. To the mixture is added 8M NaOH (11.5 mL) at room temperature and the mixture is stirred for 2 h. After the addition of 5% NaCl (400 mL) and AcOEt (800 mL), the organic layer is separated. The organic layer is washed with 5% NaCl (400 mL) twice. The organic layer is concentrated to 240 mL. After the addition of MeOH (800 mL), the mixture is concentrated to 240 mL. After the addition of MeOH (800 mL), the mixture is concentrated to 240 mL. After the addition of MeOH (160 mL), the mixture is stirred at room temperature for 1 h and at 0° C. for 1 h. The crystals are isolated by filtration, washed with cold MeOH (160 mL) and dried to give (6aR,9aS)-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one (55.7 g). $^1$H NMR (500 MHz, CDCl$_3$) δ 1.39-1.54 (m, 1H), 1.58-1.81 (m, 3H), 1.81-1.92 (m, 1H), 2.12-2.22 (m, 1H), 3.28 (s, 3H), 4.61-4.70 (m, 2H), 5.20 (s, 2H), 6.79-6.85 (m, 1H), 7.25-7.32 (m, 2H), 7.53-7.58 (m, 1H), 7.68 (s, 1H), 7.75-7.83 (m, 1H), 7.92-7.98 (m, 2H).

(6aR,9aS)-3-chloro-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one

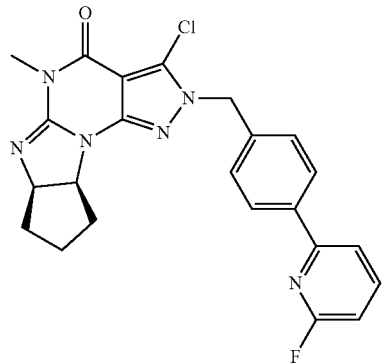 [SMILES: CN1C(=O)c2c(nn(Cc3ccc(-c4cccc(F)n4)cc3)c2Cl)N2C1=N[C@@H]1CCC[C@@H]12]

The mixture of (6aR,9aS)-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one (50 g) and toluene (1000 mL) is concentrated to 750 mL under the nitrogen atmosphere. Toluene (250 mL) and NCS (24 g) is added. To the mixture is added LiHMDS (1M THF solution, 204 mL) at 0° C. and the mixture is stirred for 0.5 h. To the mixture is added 20% NH$_4$Cl (50 mL) at 5° C. The mixture is concentrated to 250 mL. After the addition of EtOH (250 mL), the mixture is concentrated to 150 mL. After the addition of EtOH (250 mL), the mixture is concentrated to 200 mL. After the addition of EtOH (200 mL), the mixture is warmed to 50° C. Water (300 mL) is added and the mixture is stirred at 50° C. for 0.5 h. After stirring at room temperature for 1 h, the crystals are isolated by filtration, washed with the mixture of EtOH and water (1:1, 150 mL) and dried to give (6aR,9aS)-3-chloro-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one (51.1 g). $^1$H NMR (500 MHz, CDCl$_3$) δ 1.46-1.61 (m, 1H), 1.67-1.90 (m, 3H), 1.92-2.00 (m, 1H), 2.19-2.27 (m, 1H), 3.37 (s, 3H), 4.66-4.77 (m, 2H), 5.34 (s, 2H), 6.87-6.93 (m, 1H), 7.35-7.41 (m, 2H), 7.59-7.65 (m, 1H), 7.82-7.91 (m, 1H), 7.97-8.05 (m, 2H).

Example 1

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one Free Base mono-ethanol Solvate

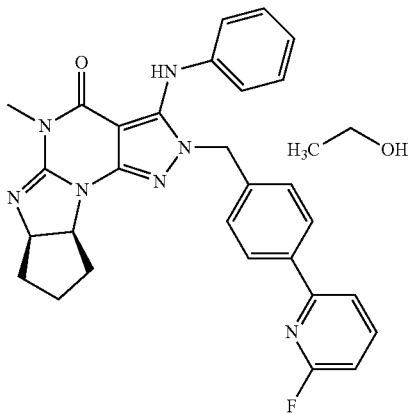

The mixture of (6aR,9aS)-3-chloro-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one (2.5 g), K$_2$CO$_3$ (1.53 g), Pd(OAc)$_2$ (12.5 mg), Xantphos (32 mg), aniline (0.76 mL), and xylene (12.5 mL) is stirred at 125° C. for 7 h under nitrogen atmosphere. After addition of water (12.5 mL), the organic layer is separated. The organic layer is washed with water (12.5 mL) twice. The organic layer is extracted with the mixture of DMAc (6.25 mL) and 0.5N HCl (12.5 mL). The organic layer is extracted with the mixture of DMAc (3.2 mL) and 0.5N HCl (6.25 mL). After addition of DMAc (6.25 mL), xylene (12.5 mL) and 25 wt % aqueous NH$_3$ solution to the combined aqueous layer, the organic layer is separated. The aqueous layer is extracted with xylene (6.25 mL). The combined organic layer is washed with water (12.5 mL), 2.5 wt % aqueous 1,2-cyclohexanediamine solution (12.5 mL) twice and water (12.5 mL) successively. After treatment with active charcoal, the organic layer is concentrated. After addition of EtOH (12.5 mL), the mixture is concentrated. After addition of EtOH (12.5 mL), the mixture is concentrated. After addition of EtOH (12.5 mL), n-heptane (25 mL) is added at 70° C. The mixture is cooled to 5° C. and stirred at same temperature. The crystals are isolated by filtration and dried to give (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base mono-ethanol solvate (2.56 g) as crystals.

$^1$H NMR (500 MHz, DMSO-d$_6$) δ 0.98-1.13 (m, 3H), 1.34-1.52 (m, 1H), 1.54-1.83 (m, 4H), 2.03-2.17 (m, 1H), 3.11 (s, 3H), 3.39-3.54 (m, 2H), 4.29-4.43 (m, 1H), 4.51-4.60 (m, 1H), 4.60-4.70 (m, 1H), 5.15-5.35 (m, 2H), 6.71-6.88 (m, 3H), 7.05-7.29 (m, 5H), 7.81-7.93 (m, 1H), 7.94-8.11 (m, 3H), 8.67 (s, 1H).

The Differential Scanning calorimetry (DSC) thermograph of mono-ethanol solvate free base crystals are obtained as described or similarly described herein and the DSC is depicted in FIG. 1-A. Approximately 2 mg of sample is weighed into an aluminum DSC pan and sealed hermetic lid (crimped). The sample is then loaded into a Hitachi High-Tech DSC6220ASD-2 at 30° C. The sample is heated from 30 to 250° C. at scan rate of 5° C./min and the resulting heat flow response is monitored. A 50 mL/min nitrogen purge is used to prevent thermally induced oxidation of the sample during heating and to reduce the thermal lag through the sample to increase the instrument sensitivity.

The XRPD of mono-ethanol solvate free base crystals is obtained as described or similarly described herein. The result is depicted in FIG. 1-B. Approximately 20 mg of sample is gently put on the XRPD glass sample holder. The sample is then loaded into a MiniFlex II and analyzed using the following experimental conditions.

Tube anode: Cu

Generator tension: 30 kV

Tube current: 15 mA

Wavelength alpha 1: 1.5406 A

Wavelength alpha 2: 1.5444 A

Start angle [2 theta]: 3

End angle [2 theta]: 40

Scan speed 6.000°/min

Scan step size: 0.02

The XRPD pattern of the mono-ethanol solvate crystals is depicted in FIG. 1-B and has peaks as set forth in Table 1 below:

TABLE 1

| No | Pos. [°2Th.] | d-spacing [Å] | Height [cps] | Rel. Int. [%] |
|---|---|---|---|---|
| 1 | 6.16 | 14.3361 | 15985 | 100 |
| 2 | 7.58 | 11.6533 | 7985 | 50 |
| 3 | 8.16 | 10.8263 | 6641 | 42 |
| 4 | 11.18 | 7.9077 | 890 | 6 |
| 5 | 12.36 | 7.1553 | 3411 | 22 |
| 6 | 12.84 | 6.8888 | 2076 | 13 |
| 7 | 13.42 | 6.5924 | 2257 | 15 |
| 8 | 15.20 | 5.8241 | 4004 | 26 |
| 9 | 16.48 | 5.3746 | 433 | 3 |
| 10 | 17.62 | 5.0293 | 1692 | 11 |
| 11 | 18.22 | 4.8650 | 6533 | 41 |
| 12 | 19.10 | 4.6428 | 8513 | 54 |
| 13 | 19.78 | 4.4847 | 6436 | 41 |
| 14 | 20.98 | 4.2308 | 5242 | 33 |
| 15 | 21.90 | 4.0551 | 3182 | 20 |
| 16 | 22.58 | 3.9345 | 9727 | 61 |
| 17 | 23.10 | 3.8471 | 751 | 5 |
| 18 | 23.72 | 3.7479 | 1621 | 11 |
| 19 | 24.78 | 3.5900 | 2058 | 13 |
| 20 | 25.78 | 3.4529 | 2825 | 18 |
| 21 | 26.56 | 3.3533 | 1085 | 7 |
| 22 | 27.76 | 3.2110 | 5312 | 34 |
| 23 | 28.44 | 3.1357 | 1078 | 7 |
| 24 | 29.64 | 3.0115 | 2655 | 17 |
| 25 | 30.94 | 2.8878 | 807 | 6 |
| 26 | 31.82 | 2.8099 | 352 | 3 |
| 27 | 32.60 | 2.7445 | 321 | 2 |
| 28 | 33.40 | 2.6805 | 411 | 3 |
| 29 | 34.26 | 2.6152 | 951 | 6 |
| 30 | 36.28 | 2.4741 | 278 | 2 |
| 31 | 37.18 | 2.4162 | 302 | 2 |
| 32 | 38.36 | 2.3446 | 384 | 3 |
| 33 | 39.52 | 2.2784 | 224 | 2 |

Example 1-B

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one Free Base mono-ethanol Solvate

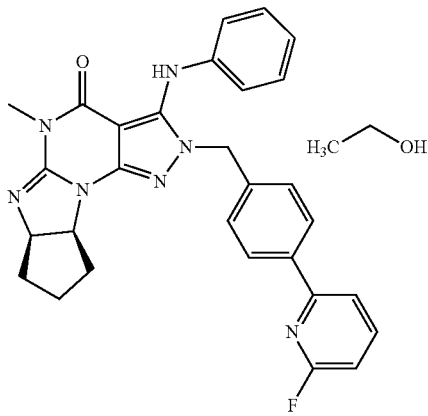

31 mg of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base is dissolved in 1 mL of ethanol. The solution is sonicated for 10 seconds and instant precipitation of white solids is observed. The solids are filtered using vacuum filtration and then air dried.

The Differential Scanning calorimetry (DSC) thermograph and the thermogravimetric analysis (TGA) of the mono-ethanol solvate crystals is obtained as described or similarly described herein and the DSC and TGA is depicted in FIG. 6-B.

DSC: Approximately, 4 mg of sample is weighed into an aluminium DSC pan. The sample is then loaded into a Perkin-Elmer Jade DSC at −10° C. The sample is heated from −10° C. to 90° C. at various scan rates (1° C./min and 50° C./min) and resulting heat flow response is monitored. A 20 cm³/min nitrogen purge is used to prevent thermally induced oxidation of the sample during heating and to reduce the thermal lag through the sample to increase the instrument sensitivity. Prior to analysis, the instrument is temperature and heat-flow calibrated using an indium reference standard.

TGA: Approximately 5 mg of sample is accurately weighed into a ceramic crucible and it is placed into the chamber of Perkin-Elmer STA 600 TGA/DTA analyzer at ambient temperature. The sample is then heated at a rate of 10° C./min from 25° C. to 350° C. during which time the change in weight monitored as well as DTA signal. The purge gas used is nitrogen at a flow rate of 20 cm3/min Prior to analysis the instrument is weight calibrated using a 100 mg reference weight and temperature calibrated using an indium reference standard.

The X-ray powder diffraction pattern of the solids is obtained by using a method described or similarly described herein and the XRPD is depicted in FIG. 6-A. Approximately 20 mg of sample is gently compressed on the XRPD zero back ground single obliquely cut silica sample holder. The sample is then loaded into a Philips X-Pert PRO diffractometer and analyzed using the following experimental conditions:
Tube anode: Cu
Generator tension: 40 kV
Tube current: 40 mA
Wavelength alpha1: 1.5406 Å
Wavelength alpha2: 1.5444 Å
Start angle [2 theta]: 4
End angle [2 theta]: 40
Time per step: 2.5 seconds
Scan step size: 0.016

Example 2

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one Free Base mono-n-propanol Solvate

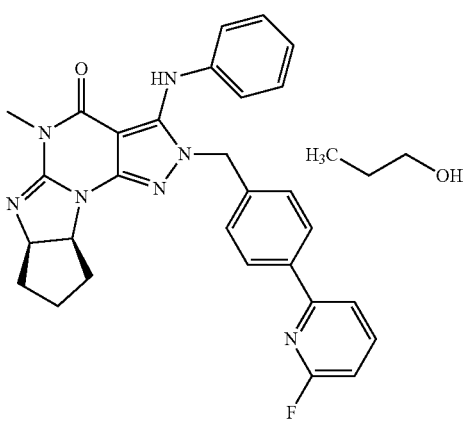

The mixture of (6aR,9aS)-3-chloro-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one (10 g), K₂CO₃ (6.14 g), Pd(OAc)₂ (50 mg), Xantphos (128 mg), aniline (3.04 mL), DMAc (5 mL) and xylene (50 mL) is stirred at 125° C. for 5 h under nitrogen atmosphere. After addition of water (50 mL), the organic layer is separated. The organic layer is washed with the mixture of DMAc (25 mL) and water (50 mL) twice. The organic layer is extracted with the mixture of DMAc (25 mL) and 0.5N HCl (50 mL). The organic layer is extracted with the mixture of DMAc (12.5 mL) and 0.5N HCl (25 mL). After addition of DMAc (25 mL), xylene (50 mL) and 25 wt % aqueous NH₃ solution to the combined aqueous layer, the organic layer is separated. The aqueous layer is extracted with xylene (25 mL). The combined organic layer is washed with water (50 mL), 2.5 wt % aqueous 1,2-cyclohexanediamine solution (50 mL) twice and water (50 mL) successively. After treatment with active charcoal, the organic layer (300 g) is obtained. The organic layer (60 g) is measured and concentrated. After addition of n-propanol, the mixture is concentrated. After addition of n-propanol (10 mL), n-heptane (10 mL) is added at 90° C. The mixture is cooled to room temperature. The crystals are isolated by filtration and dried to give (6aR,9aS)-5,6a,7,8,9,9a-hexahydro-5-methyl-3-(phenylamino)-2-((4-(6-fluoropyridin-2-yl)phenyl)

methyl)-cyclopent[4,5]imidazo[1,2-a]pyrazolo[4,3-e]pyrimidin-4(2H)-one free base mono-n-propanol solvate (2.23 g) as crystals.

$^1$H NMR (500 MHz, DMSO-d$_6$) δ 0.74-0.92 (m, 3H), 1.31-1.50 (m, 3H), 1.54-1.83 (m, 4H), 1.98-2.21 (m, 1H), 3.11 (s, 3H), 3.25-3.42 (m, 2H), 4.29-4.43 (m, 1H), 4.51-4.60 (m, 1H), 4.60-4.70 (m, 1H), 5.15-5.35 (m, 2H), 6.71-6.88 (m, 3H), 7.05-7.29 (m, 5H), 7.81-7.93 (m, 1H), 7.94-8.11 (m, 3H), 8.66 (s, 1H).

The Differential Scanning calorimetry (DSC) thermograph of mono-n-propanol solvate free base crystals is obtained as described or similarly described herein and the DSC is depicted in FIG. 2-A. Approximately 3 mg of sample is weighed into an aluminum DSC pan and sealed hermetic lid (crimped). The sample is then loaded into a Hitachi High-Tech DSC6220ASD-2 at 30° C. The sample is heated from 30 to 250° C. at scan rate of 5° C./min and the resulting heat flow response is monitored. A 50 mL/min nitrogen purge is used to prevent thermally induced oxidation of the sample during heating and to reduce the thermal lag through the sample to increase the instrument sensitivity.

The XRPD of the mono-n-propanol solvate free base crystals is obtained as described or similarly described herein. The result is depicted in FIG. 2-B. Approximately 20 mg of sample is gently put on the XRPD glass sample holder. The sample is then loaded into a MiniFlex II and analyzed using the following experimental conditions.
Tube anode: Cu
Generator tension: 30 kV
Tube current: 15 mA
Wavelength alpha 1: 1.5406 A
Wavelength alpha 2: 1.5444 A
Start angle [2 theta]: 3
End angle [2 theta]: 40
Scan speed 6.000°/min
Scan step size: 0.02
The XRPD pattern of the mono-n-propanol solvate free base crystals is depicted in FIG. 2-B and has peaks as set forth in Table 2 below:

TABLE 2

| No | Pos. [°2Th.] | d-spacing [Å] | Height [cps] | Rel. Int. [%] |
|---|---|---|---|---|
| 1 | 6.02 | 14.6692 | 4134 | 22 |
| 2 | 7.56 | 11.6841 | 6333 | 33 |
| 3 | 8.06 | 10.9604 | 6419 | 33 |
| 4 | 11.12 | 7.9502 | 1717 | 9 |
| 5 | 11.96 | 7.3937 | 1495 | 8 |
| 6 | 12.12 | 7.2964 | 2064 | 11 |
| 7 | 13.00 | 6.8044 | 3750 | 20 |
| 8 | 15.14 | 5.8471 | 5302 | 28 |
| 9 | 15.90 | 5.5693 | 958 | 5 |
| 10 | 16.34 | 5.4203 | 458 | 3 |
| 11 | 18.24 | 4.8597 | 6917 | 36 |
| 12 | 19.26 | 4.6046 | 19500 | 100 |
| 13 | 20.36 | 4.3582 | 2351 | 13 |
| 14 | 20.96 | 4.2348 | 7782 | 40 |
| 15 | 21.46 | 4.1373 | 2813 | 15 |
| 16 | 22.06 | 4.0261 | 4378 | 23 |
| 17 | 22.50 | 3.9483 | 6583 | 34 |
| 18 | 23.26 | 3.8210 | 547 | 3 |
| 19 | 23.96 | 3.7109 | 2333 | 12 |
| 20 | 25.32 | 3.5146 | 2052 | 11 |
| 21 | 25.76 | 3.4556 | 2554 | 14 |
| 22 | 26.70 | 3.3360 | 2694 | 14 |
| 23 | 27.64 | 3.2247 | 4917 | 26 |
| 24 | 28.80 | 3.0974 | 394 | 3 |
| 25 | 29.56 | 3.0194 | 2188 | 12 |
| 26 | 30.34 | 2.9436 | 867 | 5 |
| 27 | 30.66 | 2.9136 | 584 | 3 |
| 28 | 31.28 | 2.8572 | 1166 | 6 |
| 29 | 32.26 | 2.7726 | 466 | 3 |
| 30 | 34.14 | 2.6241 | 549 | 3 |
| 31 | 35.12 | 2.5531 | 970 | 5 |
| 32 | 35.78 | 2.5075 | 403 | 3 |
| 33 | 37.16 | 2.4175 | 346 | 2 |
| 34 | 38.54 | 2.3340 | 403 | 3 |

Example 3

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one Free Base mono-isopropanol Solvate

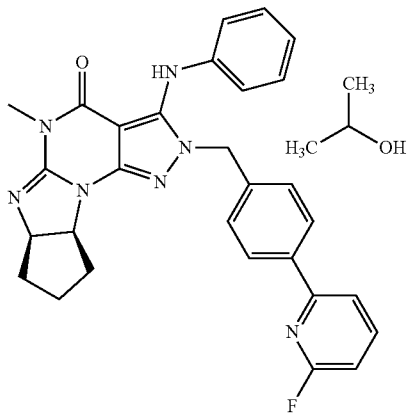

The mixture of (6aR,9aS)-3-chloro-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one (10 g), K$_2$CO$_3$ (6.14 g), Pd(OAc)$_2$ (50 mg), Xantphos (128 mg), aniline (3.04 mL), DMAc (5 mL) and xylene (50 mL) is stirred at 125° C. for 5 h under nitrogen atmosphere. After addition of water (50 mL), the organic layer is separated. The organic layer is washed with the mixture of DMAc (25 mL) and water (50 mL) twice. The organic layer is extracted with the mixture of DMAc (25 mL) and 0.5N HCl (50 mL). The organic layer is extracted with the mixture of DMAc (12.5 mL) and 0.5N HCl (25 mL). After addition of DMAc (25 mL), xylene (50 mL) and 25 wt % aqueous NH$_3$ solution to the combined aqueous layer, the organic layer is separated. The aqueous layer is extracted with xylene (25 mL). The combined organic layer is washed with water (50 mL), 2.5 wt % aqueous 1,2-cyclohexanediamine solution (50 mL) twice and water (50 mL) successively. After treatment with active charcoal, the organic layer (300 g) is obtained. The organic layer (60 g) is measured and concentrated. After addition of 2-propanol, the mixture is concentrated. After addition of 2-propanol (10 mL), n-heptane (20 mL) is added at 70° C. The mixture is cooled to room temperature. The crystals are isolated by filtration and dried to give (6aR,9aS)-5,6a,7,8,9,9a-hexahydro-5-methyl-3-(phenylamino)-2-((4-(6-fluoropyridin-2-yl)phenyl)-methyl)-cyclopent[4,5]imidazo[1,2-a]pyrazolo[4,3-e]pyrimidin-4(2H)-one free base mono-isopropanol solvate (2.13 g) as crystals.

¹H NMR (500 MHz, DMSO-d₆) δ 1.04 (d, 6H, J=5.99 Hz), 1.30-1.50 (m, 1H), 1.51-1.83 (m, 4H), 1.99-2.20 (m, 1H), 3.11 (s, 3H), 3.72-3.88 (m, 1H), 4.28-4.40 (m, 1H), 4.50-4.60 (m, 1H), 4.60-4.70 (m, 1H), 5.15-5.32 (m, 2H), 6.71-6.91 (m, 3H), 7.01-7.30 (m, 5H), 7.84-7.94 (m, 1H), 7.94-8.12 (m, 3H), 8.65 (s, 1H).

The Differential Scanning calorimetry (DSC) thermograph of mono-isopropanol solvate free base crystals is obtained as described or similarly described herein and the DSC is depicted in FIG. 3-A. Approximately 2 mg of sample is weighed into an aluminum DSC pan and sealed hermetic lid (crimped). The sample is then loaded into a Hitachi High-Tech DSC6220ASD-2 at 30° C. The sample is heated from 30 to 250° C. at scan rate of 5° C./min and the resulting heat flow response is monitored. A 50 mL/min nitrogen purge is used to prevent thermally induced oxidation of the sample during heating and to reduce the thermal lag through the sample to increase the instrument sensitivity.

The XRPD of mono-isoprpanol solvate free base crystals is obtained as described or similarly described herein. The result is depicted in FIG. 3-B. Approximately 20 mg of sample is gently put on the XRPD glass sample holder. The sample is then loaded into a MiniFlex II and analyzed using the following experimental conditions.

Tube anode: Cu
Generator tension: 30 kV
Tube current: 15 mA
Wavelength alpha 1: 1.5406 A
Wavelength alpha 2: 1.5444 A
Start angle [2 theta]: 3
End angle [2 theta]: 40
Scan speed 6.000°/min
Scan step size: 0.02

The XRPD pattern of mono-isopropanol solvate free base crystals is depicted in FIG. 3-B and has peaks as set forth in Table 3 below:

TABLE 3

| No | Pos. [°2Th.] | d-spacing [Å] | Height [cps] | Rel. Int. [%] |
|---|---|---|---|---|
| 1 | 6.02 | 14.6692 | 8237 | 71 |
| 2 | 7.66 | 11.5318 | 5866 | 51 |
| 3 | 8.18 | 10.7998 | 5708 | 49 |
| 4 | 11.12 | 7.9502 | 2294 | 20 |
| 5 | 12.20 | 7.2487 | 3111 | 27 |
| 6 | 12.76 | 6.9318 | 2968 | 26 |
| 7 | 13.42 | 6.5924 | 2363 | 21 |
| 8 | 14.88 | 5.9487 | 4043 | 35 |
| 9 | 15.36 | 5.7638 | 6270 | 54 |
| 10 | 16.36 | 5.4137 | 913 | 8 |
| 11 | 18.24 | 4.8597 | 11094 | 95 |
| 12 | 18.94 | 4.6817 | 11691 | 100 |
| 13 | 19.84 | 4.4713 | 7080 | 61 |
| 14 | 20.50 | 4.3288 | 2855 | 25 |
| 15 | 20.92 | 4.2428 | 5215 | 45 |
| 16 | 21.86 | 4.0625 | 5015 | 43 |
| 17 | 22.48 | 3.9518 | 9259 | 80 |
| 18 | 23.22 | 3.8275 | 2798 | 24 |
| 19 | 24.66 | 3.6072 | 2542 | 22 |
| 20 | 25.90 | 3.4372 | 3343 | 29 |
| 21 | 26.54 | 3.3558 | 918 | 8 |
| 22 | 27.46 | 3.2454 | 4116 | 36 |
| 23 | 27.92 | 3.1929 | 2252 | 20 |
| 24 | 29.60 | 3.0154 | 1911 | 17 |
| 25 | 30.18 | 2.9588 | 1085 | 10 |
| 26 | 31.12 | 2.8715 | 837 | 8 |
| 27 | 32.30 | 2.7693 | 493 | 5 |
| 28 | 33.02 | 2.7105 | 536 | 5 |
| 29 | 34.10 | 2.6271 | 1400 | 12 |
| 30 | 34.70 | 2.5830 | 251 | 3 |
| 31 | 35.42 | 2.5322 | 568 | 5 |
| 32 | 36.22 | 2.4780 | 371 | 4 |
| 33 | 37.72 | 2.3829 | 209 | 2 |
| 34 | 38.30 | 2.3481 | 296 | 3 |
| 35 | 38.82 | 2.3178 | 304 | 3 |

Example 4

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one Free Base Non-Solvate

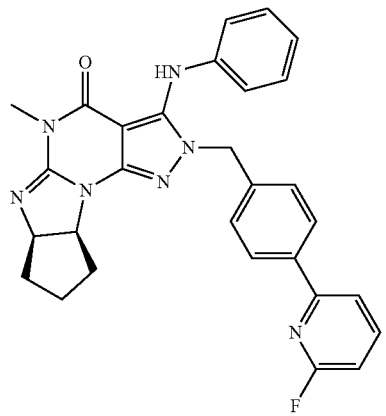 [SMILES: CN1C(=O)c2c(nn(Cc3ccc(-c4cccc(F)n4)cc3)c2Nc2ccccc2)N2C1=N[C@@H]1CCC[C@@H]12]

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base mono-n-propanol solvate (2.0 g) is dissolved with ethanol (10 mL) at 70° C. Isopropyl ether (20 mL) is added and the mixture is cooled to 45° C. Isopropyl ether (10 mL) is added and the mixture is stirred at 40° C. The mixture is cooled to 5° C. and stirred at same temperature. The crystals are isolated by filtration and dried to give (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base non-solvate (1.7 g) as crystals.

¹H NMR (500 MHz, DMSO-d₆) δ 1.32-1.51 (m, 1H), 1.53-1.83 (m, 4H), 1.97-2.20 (m, 1H), 3.11 (s, 3H), 4.49-4.60 (m, 1H), 4.60-4.69 (m, 1H), 5.13-5.37 (m, 2H), 6.70-6.90 (m, 3H), 7.04-7.31 (m, 5H), 7.82-7.93 (m, 1H), 7.93-8.12 (m, 3H), 8.67 (s, 1H).

The Differential Scanning calorimetry (DSC) thermograph of non-solvate free base crystals is obtained as described or similarly described herein and the DSC is depicted in FIG. 4-A. Approximately 3 mg of sample is weighed into an aluminum DSC pan and sealed hermetic lid (crimped). The sample is then loaded into a Hitachi High-Tech DSC6220ASD-2 at 30° C. The sample is heated from 30 to 250° C. at scan rate of 5° C./min and the resulting heat flow response is monitored. A 50 mL/min nitrogen purge is used to prevent thermally induced oxidation of the sample during heating and to reduce the thermal lag through the sample to increase the instrument sensitivity.

The XRPD of non-solvate free base crystals is obtained as described or similarly described herein. The result is depicted in FIG. 4-B. Approximately 20 mg of sample is gently put on the XRPD glass sample holder. The sample is then loaded into a MiniFlex II and analyzed using the following experimental conditions.

Tube anode: Cu
Generator tension: 30 kV
Tube current: 15 mA
Wavelength alpha 1: 1.5406 A
Wavelength alpha 2: 1.5444 A
Start angle [2 theta]: 3
End angle [2 theta]: 40
Scan speed 6.000°/min
Scan step size: 0.02

The XRPD pattern of non-solvate free base crystals is depicted in FIG. 4-B and has peaks as set forth in Table 4 below:

TABLE 4

| No | Pos. [°2Th.] | d-spacing [Å] | Height [cps] | Rel. Int. [%] |
|---|---|---|---|---|
| 1 | 4.62 | 19.1107 | 273 | 2 |
| 2 | 7.06 | 12.5104 | 4683 | 31 |
| 3 | 7.74 | 11.4128 | 15123 | 100 |
| 4 | 8.02 | 11.0149 | 10678 | 71 |
| 5 | 9.22 | 9.5838 | 1208 | 8 |
| 6 | 9.88 | 8.9451 | 2099 | 14 |
| 7 | 10.52 | 8.4023 | 289 | 2 |
| 8 | 13.40 | 6.6022 | 2653 | 18 |
| 9 | 13.88 | 6.3749 | 1553 | 11 |
| 10 | 14.52 | 6.0953 | 305 | 3 |
| 11 | 15.42 | 5.7415 | 511 | 4 |
| 12 | 16.62 | 5.3296 | 1391 | 10 |
| 13 | 17.28 | 5.1275 | 4822 | 32 |
| 14 | 18.34 | 4.8335 | 2675 | 18 |
| 15 | 19.44 | 4.5624 | 1600 | 11 |
| 16 | 20.20 | 4.3924 | 1250 | 9 |
| 17 | 21.34 | 4.1603 | 6007 | 40 |
| 18 | 22.70 | 3.9140 | 2330 | 16 |
| 19 | 23.30 | 3.8145 | 3311 | 22 |
| 20 | 24.88 | 3.5758 | 2363 | 16 |
| 21 | 26.44 | 3.3682 | 627 | 5 |
| 22 | 27.32 | 3.2617 | 441 | 3 |
| 23 | 28.28 | 3.1531 | 667 | 5 |
| 24 | 29.42 | 3.0335 | 393 | 3 |
| 25 | 30.04 | 2.9723 | 269 | 2 |
| 26 | 31.18 | 2.8661 | 433 | 3 |
| 27 | 31.42 | 2.8448 | 515 | 4 |

Example 5

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one Free Base Non-Solvate

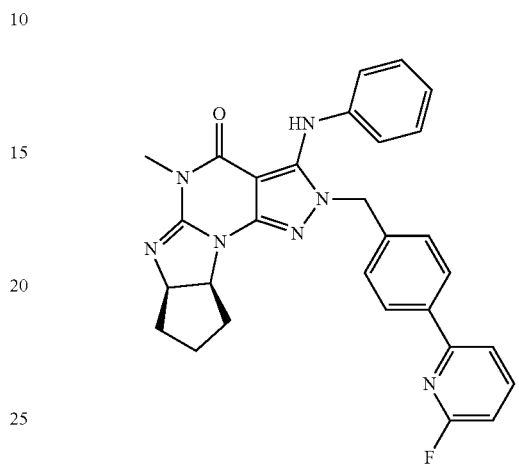

The mixture of (6aR,9aS)-3-chloro-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one (25 g), $K_2CO_3$ (15.4 g), Pd(OAc)$_2$ (125 mg), Xantphos (321 mg), aniline (7.6 mL), DMAc (6.25 mL) and xylene (125 mL) is stirred at 125° C. for 6.5 h under nitrogen atmosphere. After addition of water (125 mL) and DMAc (50 mL), the organic layer is separated. The organic layer is washed with the mixture of DMAc (50 mL) and water (125 mL) twice. The organic layer is extracted with the mixture of DMAc (50 mL) and 0.5N HCl (125 mL). The organic layer is extracted with the mixture of DMAc (50 mL) and 0.5N HCl (62.5 mL). After addition of DMAc (50 mL), xylene (125 mL) and 25 wt % aqueous $NH_3$ solution (25 mL) to the combined aqueous layer, the organic layer is separated. The aqueous layer is extracted with xylene (62.5 mL). The combined organic layer is washed with the mixture of DMAc (50 mL) and water (125 mL), the mixture of DMAc (50 mL) and 2.5 wt % aqueous 1,2-cyclohexanediamine solution (125 mL) twice and the mixture of DMAc (50 mL) and water (125 mL) successively. After treatment with active charcoal (1.25 g), the organic layer is concentrated to 75 mL. After addition of EtOH (125 mL), the mixture is concentrated to 75 mL. After addition of EtOH (125 mL), the mixture is concentrated to 75 mL. After addition of EtOH (125 mL), n-heptane (250 mL) is added at 70° C. After addition of seed crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one non-solvate, the mixture is cooled to room temperature and stirred at room temperature. The crystals are isolated by filtration and dried to give (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo-[1,2-a]pyrazolo[4,3-e]pyrimidin-4(2H)-one free base non-solvate (23.8 g) as crystals.

Example 6

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one Free Base Mono-Methanol Solvate

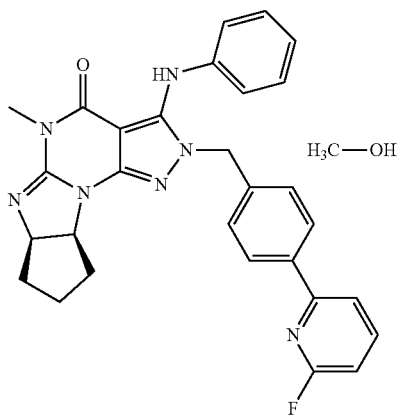

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base mono-ethanol solvate (10 g) are dissolved with toluene (60 mL) at room temperature. The mixture is concentrated. After addition of methanol (60 mL), the mixture is concentrated. After addition of methanol (60 mL), the mixture is concentrated. After addition of methanol (70 mL), the mixture is stirred at 40° C. for 1 h. The mixture is cooled to room temperature and stirred at same temperature. The crystals are isolated by filtration and dried to give (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base mono-methanol solvate (6.9 g) as crystals.

$^1$H NMR (500 MHz, DMSO-$d_6$) δ 1.34-1.51 (m, 1H), 1.52-1.80 (m, 4H), 2.02-2.16 (m, 1H), 3.12 (s, 3H), 3.18 (d, 3H, J=5.36 Hz), 4.10 (q, 1H, J=5.36 Hz), 4.52-4.59 (m, 1H), 4.60-4.69 (m, 1H), 5.14-5.32 (m, 2H), 6.74-6.85 (m, 3H), 7.08-7.27 (m, 5H), 7.85-7.93 (m, 1H), 7.93-8.10 (m, 3H), 8.65 (s, 1H).

The Differential Scanning calorimetry (DSC) thermograph of mono-methanol solvate free base crystals are obtained as described or similarly described herein and the DSC is depicted in FIG. 5-A. Approximately 3 mg of sample is weighed into an aluminum DSC pan and sealed hermetic lid (crimped). The sample is then loaded into a Hitachi High-Tech DSC6220ASD-2 at 30° C. The sample is heated from 30° to 250° C. at scan rate of 5° C./min and the resulting heat flow response is monitored. A 50 mL/min nitrogen purge is used to prevent thermally induced oxidation of the sample during heating and to reduce the thermal lag through the sample to increase the instrument sensitivity.

The XRPD of mono-methanol solvate free base crystals is obtained as described or similarly described herein. The result is depicted in FIG. 5-B. Approximately 20 mg of sample is gently put on the XRPD glass sample holder. The sample is then loaded into a MiniFlex II and analyzed using the following experimental conditions.

Tube anode: Cu

Generator tension: 30 kV

Tube current: 15 mA

Wavelength alpha 1: 1.5406 A

Wavelength alpha 2: 1.5444 A

Start angle [2 theta]: 3

End angle [2 theta]: 40

Scan speed 6.000°/min

Scan step size: 0.02

The XRPD pattern of the mono-methanol solvate free base crystals is depicted in FIG. 5-B and has peaks as set forth in Table 5 below:

TABLE 5

| No | Pos. [°2Th.] | d-spacing [Å] | Height [cps] | Rel. Int. [%] |
|---|---|---|---|---|
| 1 | 7.02 | 12.5816 | 13378 | 75 |
| 2 | 8.22 | 10.7474 | 10588 | 59 |
| 3 | 9.94 | 8.8912 | 2364 | 14 |
| 4 | 11.40 | 7.7556 | 2380 | 14 |
| 5 | 12.02 | 7.3569 | 1560 | 9 |
| 6 | 12.72 | 6.9536 | 1637 | 10 |
| 7 | 13.46 | 6.5729 | 2246 | 13 |
| 8 | 14.52 | 6.0953 | 3243 | 18 |
| 9 | 16.10 | 5.5005 | 18007 | 100 |
| 10 | 17.18 | 5.1571 | 922 | 6 |
| 11 | 18.72 | 4.7362 | 3803 | 22 |
| 12 | 19.86 | 4.4668 | 7203 | 40 |
| 13 | 21.54 | 4.1221 | 2741 | 16 |
| 14 | 22.44 | 3.9588 | 5449 | 31 |
| 15 | 22.94 | 3.8736 | 3705 | 21 |
| 16 | 23.42 | 3.7953 | 4840 | 27 |
| 17 | 23.90 | 3.7201 | 4152 | 24 |
| 18 | 24.48 | 3.6333 | 1443 | 9 |
| 19 | 25.64 | 3.4715 | 1382 | 8 |
| 20 | 26.76 | 3.3287 | 2692 | 15 |
| 21 | 27.42 | 3.2500 | 2463 | 14 |
| 22 | 28.44 | 3.1357 | 3887 | 22 |
| 23 | 29.16 | 3.0599 | 1027 | 6 |
| 24 | 29.88 | 2.9878 | 603 | 4 |
| 25 | 30.68 | 2.9117 | 365 | 3 |
| 26 | 31.30 | 2.8554 | 329 | 2 |
| 27 | 31.86 | 2.8065 | 446 | 3 |
| 28 | 32.16 | 2.7810 | 477 | 3 |
| 29 | 34.38 | 2.6063 | 665 | 4 |
| 30 | 34.98 | 2.5630 | 856 | 5 |
| 31 | 36.32 | 2.4715 | 961 | 6 |
| 32 | 38.56 | 2.3329 | 448 | 3 |

Example 7

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one Free Base mono-n-butanol Solvate

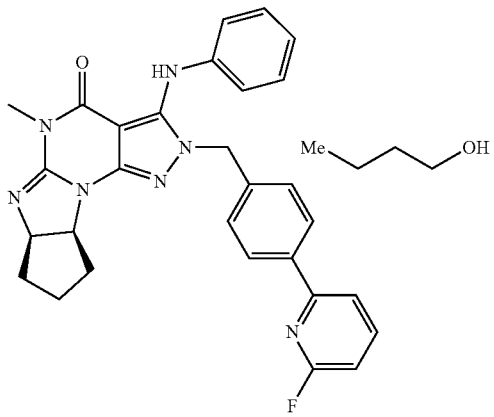

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base mono-ethanol solvate (0.5 g) are dissolved with n-butanol (3 mL) at 65° C. After addition of heptane (2 mL), the mixture is stirred at 25° C. Heptane (1 mL) is added and the mixture is stirred at 5° C. The crystals are isolated by filtration and dried to give (6aR, 9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base mono-n-butanol solvate (0.3 g) as crystals.

$^1$H NMR (500 MHz, DMSO-$d_6$) δ 0.87 (t, J=7.4 Hz, 3H), 1.25-1.48 (m, 5H), 1.54-1.78 (m, 4H), 2.00-2.20 (m, 1H), 3.11 (s, 3H), 3.30-3.42 (m, 2H), 4.29-4.32 (m, 1H), 4.51-4.60 (m, 1H), 4.60-4.70 (m, 1H), 5.19-5.30 (m, 2H), 6.71-6.90 (m, 3H), 7.05-7.25 (m, 5H), 7.81-7.93 (m, 1H), 7.94-8.10 (m, 3H), 8.64 (s, 1H).

The Differential Scanning calorimetry (DSC) thermograph of mono-n-butanol solvate free base crystals is obtained as described or similarly described herein and the DSC is depicted in FIG. 6-A. Approximately 2 mg of sample is weighed into an aluminum DSC pan and sealed hermetic lid (crimped). The sample is then loaded into a Hitachi High-Tech DSC6220ASD-2 at 30° C. The sample is heated from 30 to 250° C. at scan rate of 5° C./min and the resulting heat flow response is monitored. A 50 mL/min nitrogen purge is used to prevent thermally induced oxidation of the sample during heating and to reduce the thermal lag through the sample to increase the instrument sensitivity.

The XRPD of mono-n-butanol solvate free base crystals is obtained as described or similarly described herein. The result is depicted in FIG. 7-A. Approximately 20 mg of sample is gently put on the XRPD glass sample holder. The sample is then loaded into a MiniFlex II and analyzed using the following experimental conditions.

Tube anode: Cu
Generator tension: 30 kV
Tube current: 15 mA
Wavelength alpha 1: 1.5406 A
Wavelength alpha 2: 1.5444 A
Start angle [2 theta]: 3
End angle [2 theta]: 40
Scan speed 6.000°/min
Scan step size: 0.02

The XRPD pattern of mono-n-butanol solvate free base crystals is depicted in FIG. 7-B and has peaks as set forth in Table 6 below:

TABLE 6

| No | Pos. [°2Th.] | d-spacing [Å] | Height [cps] | Rel. Int. [%] |
|---|---|---|---|---|
| 1 | 7.06 | 12.5104 | 5115 | 36 |
| 2 | 8.18 | 10.7998 | 6755 | 48 |
| 3 | 9.88 | 8.9451 | 2095 | 15 |
| 4 | 11.36 | 7.7828 | 3285 | 24 |
| 5 | 12.14 | 7.2844 | 2975 | 21 |
| 6 | 12.76 | 6.9318 | 2960 | 21 |
| 7 | 13.36 | 6.6219 | 2305 | 17 |
| 8 | 14.42 | 6.1374 | 2580 | 19 |
| 9 | 16.00 | 5.5347 | 14250 | 100 |
| 10 | 17.26 | 5.1334 | 3785 | 27 |
| 11 | 18.60 | 4.7665 | 7430 | 53 |
| 12 | 19.92 | 4.4535 | 12475 | 88 |
| 13 | 21.42 | 4.1449 | 6725 | 48 |
| 14 | 22.42 | 3.9622 | 12260 | 87 |
| 15 | 23.44 | 3.7921 | 6950 | 49 |
| 16 | 24.44 | 3.6391 | 4010 | 29 |
| 17 | 25.28 | 3.5201 | 3780 | 27 |
| 18 | 26.20 | 3.3985 | 4255 | 30 |
| 19 | 27.14 | 3.2829 | 4995 | 36 |
| 20 | 28.28 | 3.1531 | 4805 | 34 |
| 21 | 29.22 | 3.0538 | 2995 | 22 |
| 22 | 33.80 | 2.6497 | 2510 | 18 |
| 23 | 34.04 | 2.6316 | 2515 | 18 |
| 24 | 35.78 | 2.5075 | 2310 | 17 |
| 25 | 36.28 | 2.4741 | 2075 | 15 |

Example 8

(6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one mono-phosphate salt

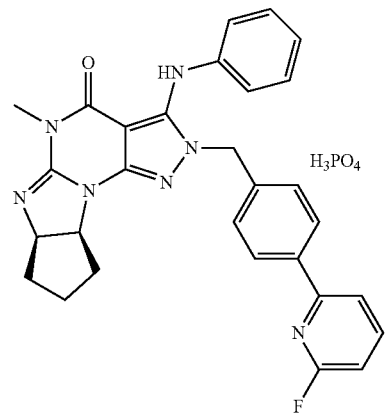

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base non-solvate (20 g) are dissolved in acetonitrile (60 mL) at 50° C. After addition of the active charcoal (1 g), the mixture is stirred at same temperature for 0.5 h. The active charcoal is removed by filtration and washed with acetonitrile (40 mL). The filtrate and the washing are combined and warmed to 50° C. A solution of 85 wt. % phosphoric acid (2.64 mL) in acetonitrile (100 mL) is added. After addition of water (20 mL), the mixture is stirred at 50° C. for 1 h. The crystals are isolated by filtration, washed with acetonitrile (60 mL×3) and dried to give (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one mono-phosphate salt (20.5 g).

Example 9

(6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one mono-phosphate salt

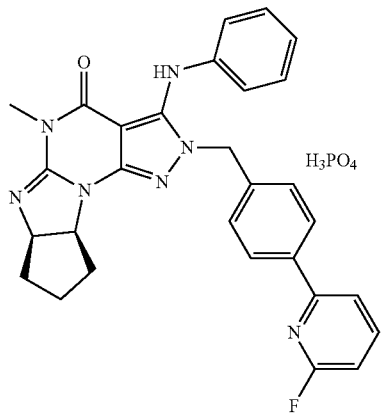

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base mono-ethanol solvate (4 g) are dissolved in acetonitrile (12 mL) at 50° C. After addition of active charcoal (0.2 g), the mixture is stirred at same temperature for 0.5 h. Active charcoal is removed by filtration and washed with acetonitrile (8 mL). The filtrate and the washing are combined and warmed to 50° C. A solution of 85 wt. % phosphoric acid (0.528 mL) in acetonitrile (20 mL) is added. After addition of water (4 mL), the mixture is stirred at 50° C. for 1 h. The crystals are isolated by filtration, washed with acetonitrile (12 mL×3) and dried to give (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one mono-phosphate salt (4.01 g).

Example 10

(6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one mono-phosphate salt

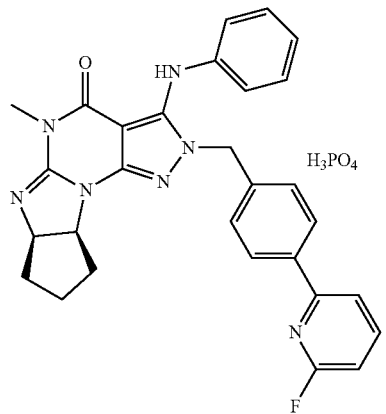

Crystals of (6aR,9aS)-5,6a,7,8,9,9a-Hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base non-solvate (20 g) are dissolved in acetone (60 mL) at 32° C. After addition of active charcoal (1 g), the mixture is stirred at same temperature for 0.5 h. Active charcoal is removed by filtration and washed with acetone (40 mL). The filtrate and the washing are combined and warmed to 39° C. A solution of 85 wt. % phosphoric acid (2.64 mL) in acetone (100 mL) is added. After addition of water (20 mL), the mixture is stirred at 40° C. for 1 h. The crystals are isolated by filtration, washed with acetone (60 mL×3) and dried to give (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one mono-phosphate salt (22.86 g).

Example 11

(6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one mono-phosphate salt

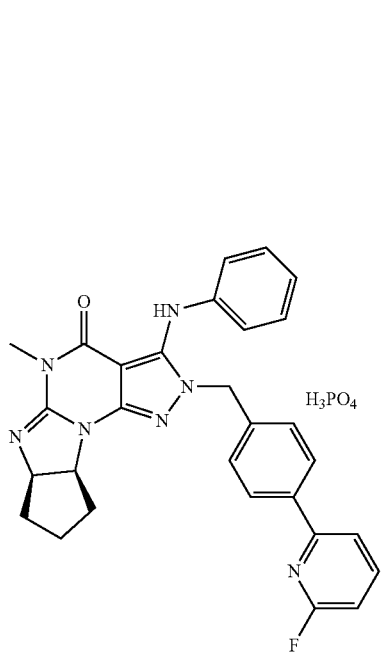

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base mono-ethanol solvate (20 g) are dissolved in acetone (60 mL) at 38° C. After addition of active charcoal (1 g), the mixture is stirred at same temperature for 0.5 h. Active charcoal is removed by filtration and washed with acetone (40 mL). The filtrate and the washing are combined and warmed to 38° C. A solution of 85 wt. % phosphoric acid (2.64 mL) in acetone (100 mL) is added. After addition of water (20 mL), the mixture is stirred at 40° C. for 1 h. The crystals are isolated by filtration, washed with acetone (60 mL×3) and dried to give (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one mono-phosphate salt (23.2 g).

Example 12

Salt Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one hemi-fumarate 0.5 ethyl acetate 0.3 acetone solvate

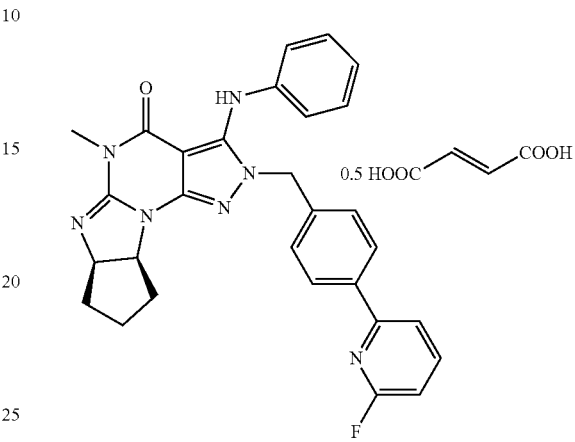

The mixture of (6aR,9aS)-3-chloro-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one (50 g), $K_2CO_3$ (30.7 g), Pd(OAc)$_2$ (249 mg), Xantphos (642 mg), aniline (15.5 g), DMAc (12.5 mL) and xylene (250 mL) is stirred at 125° C. for 6 h under nitrogen atmosphere. After addition of a solution of cystein (12.5 g) in water (250 mL), DMAc (100 mL) and xylene (50 mL), the organic layer is separated. The organic layer is extracted with the mixture of water (500 mL), DMAc (100 mL) and 12N HCl (20 mL). The aqueous layer is washed with EtOAc (375 mL). After addition of EtOAc (500 mL) and 25 wt % aqueous $NH_3$ solution (27.5 mL), the organic layer is separated. The organic layer is concentrated to 400 mL. Active charcoal (5 g) and Quadrasil MP (10 g) are added and the mixture is stirred for 2 h at 50° C. After filtration, the insoluble materials are washed with EtOAc (100 mL) and acetone (100 mL). Fumaric acid (0.64 g) is added at 40° C. After stirred for 1 h, fumaric acid (2.58 g) is added at 45° C. After stirred for 10 min, fumaric acid (1.29 g) is added at 45° C. After stirred for 10 min, fumaric acid (1.29 g) is added at 45° C. After stirred for 10 min, fumaric acid (1.29 g) is added at 45° C. The mixture is stirred at room temperature for overnight and cooled to 10° C. The mixture is stirred at same temperature for 2 h. The crystals are isolated by filtration, washed with acetone/EtOAc (1/1, 200 mL) and dried to give (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one hemi-fumarate 0.5 ethyl acetate 0.3 acetone solvate (62.76 g) as crystals.

$^1$H NMR (500 MHz, DMSO-$d_6$) δ 1.18 (t, J=7.09 Hz, 1.5H), 1.38-1.52 (m, 1H), 1.56-1.80 (m, 4H), 2.00 (s, 1.5H), 2.05-2.16 (m, 3H), 3.12 (s, 3H), 4.04 (q, J=6.94 Hz, 1H), 4.54-4.61 (m, 1H), 4.62-4.71 (m, 1H), 5.20-5.31 (m, 2H), 6.62 (s, 1H), 6.77-6.84 (m, 3H), 7.12-7.24 (m, 5H), 7.89-7.92 (m, 1H), 7.98-8.10 (m, 3H), 8.69 (s, 1H).

Differential Scanning calorimetry (DSC) thermograph of hemi-fumarate 0.5 ethyl acetate 0.3 acetone solvate salt crystals is obtained as described or similarly described herein and the DSC is depicted in FIG. 8-A. Approximately 3 mg of sample is weighed into an aluminum DSC pan and sealed hermetic lid (crimped). The sample is then loaded into a Hitachi High-Tech DSC6220ASD-2 at 30° C. The sample is heated from 30 to 250° C. at scan rate of 5° C./min and the resulting heat flow response is monitored. A 50 mL/min nitrogen purge is used to prevent thermally induced oxidation of the sample during heating and to reduce the thermal lag through the sample to increase the instrument sensitivity.

The XRPD of hemi-fumarate 0.5 ethyl acetate 0.3 acetone solvate salt crystals is obtained as described or similarly described herein. The result is depicted in FIG. 8-B. Approximately 20 mg of sample is gently put on the XRPD glass sample holder. The sample is then loaded into a MiniFlex II and analyzed using the following experimental conditions.

Tube anode: Cu

Generator tension: 30 kV

Tube current: 15 mA

Wavelength alpha 1: 1.5406 A

Wavelength alpha 2: 1.5444 A

Start angle [2 theta]: 3

End angle [2 theta]: 40

Scan speed 6.000°/min

Scan step size: 0.02

The XRPD pattern of hemi-fumarate 0.5 ethyl acetate 0.3 acetone solvate salt crystals is FIG. 8-B and has peaks as set forth in Table 7 below:

TABLE 7

| No | Pos. [°2Th.] | d-spacing [Å] | Height [cps] | Rel. Int. [%] |
|---|---|---|---|---|
| 1 | 6.02 | 14.6692 | 15506 | 100 |
| 2 | 7.38 | 11.9687 | 2374 | 16 |
| 3 | 8.04 | 10.9876 | 207 | 2 |
| 4 | 10.80 | 8.1850 | 409 | 3 |
| 5 | 11.94 | 7.4060 | 3675 | 24 |
| 6 | 12.68 | 6.9754 | 2227 | 15 |
| 7 | 13.70 | 6.4583 | 1986 | 13 |
| 8 | 14.42 | 6.1374 | 820 | 6 |
| 9 | 15.02 | 5.8935 | 630 | 5 |
| 10 | 15.84 | 5.5902 | 840 | 6 |
| 11 | 17.04 | 5.1992 | 6284 | 41 |
| 12 | 17.70 | 5.0068 | 3109 | 21 |
| 13 | 19.02 | 4.6622 | 1871 | 13 |
| 14 | 19.24 | 4.6093 | 1390 | 9 |
| 15 | 20.62 | 4.3039 | 3756 | 25 |
| 16 | 21.80 | 4.0735 | 8794 | 57 |
| 17 | 22.60 | 3.9311 | 2387 | 16 |
| 18 | 23.76 | 3.7417 | 2481 | 16 |
| 19 | 24.80 | 3.5871 | 2161 | 14 |
| 20 | 25.64 | 3.4715 | 1220 | 8 |
| 21 | 26.66 | 3.3409 | 432 | 3 |
| 22 | 27.60 | 3.2292 | 1574 | 11 |
| 23 | 29.18 | 3.0579 | 1442 | 10 |
| 24 | 29.74 | 3.0016 | 1212 | 8 |
| 25 | 30.38 | 2.9398 | 558 | 4 |
| 26 | 31.30 | 2.8554 | 323 | 3 |
| 27 | 31.94 | 2.7997 | 360 | 3 |
| 28 | 34.18 | 2.6211 | 271 | 2 |
| 29 | 35.28 | 2.5419 | 239 | 2 |
| 30 | 35.72 | 2.5116 | 281 | 2 |
| 31 | 37.46 | 2.3988 | 257 | 2 |

Example 13

Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one Free Base mono-ethanol Solvate

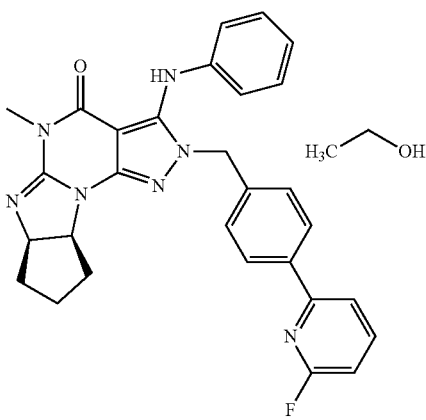

To the mixture of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one hemi-fumarate 0.5 ethyl acetate 0.3 acetone solvate salt crystal (61.63 g), EtOAc (750 mL) and water (250 mL) is added 25 wt % aqueous NH₃ solution (25 mL). The organic layer is separated and washed with water (250 mL). The organic layer is concentrated to 150 mL. After addition of EtOH (300 mL), the mixture is concentrated to 150 mL. Heptane (750 mL) is added at 50° C. and the mixture is cooled to 5° C. and stirred at the same temperature for 2 h. The crystals is isolated by filtration, washed with EtOH/heptane (1/5, 150 mL) and dried to give (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base mono-ethanol solvate (52.7 g) as crystals.

Example 14

Salt Crystals of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one benzoate

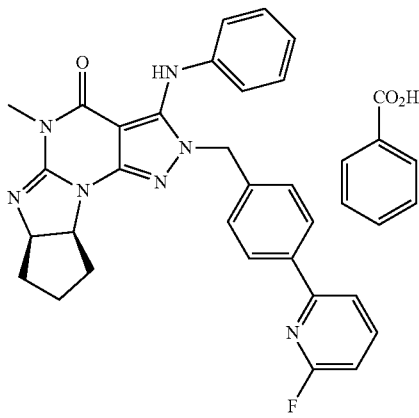

Benzoic acid (2.21 g) is added to the mixture of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base mono-ethanol solvate (5.00 g), EtOAc (25 mL) and xylene (25 mL) at room temperature. The mixture is stirred at room temperature for 6 h. The crystals are isolated by filtration, washed with EtOAc/xylene (1/1, 20 mL) and dried to give crude product. The crude product is added to acetone (50 mL) and the mixture is stirred at room temperature for 2 h. The crystals are isolated by filtration, washed with acetone (25 mL) and dried to give (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one benzoate (3.00 g) as crystals.

$^1$H NMR (500 MHz, DMSO-$d_6$) δ 1.37-1.50 (m, 1H), 1.58-1.76 (m, 4H), 2.06-2.13 (m, 1H), 3.12 (s, 3H), 4.54-4.60 (m, 1H), 4.62-4.67 (m, 1H), 5.20-5.29 (m, 2H), 6.77-6.84 (m, 3H), 7.11-7.24 (m, 5H), 7.49-7.53 (m, 2H), 7.60-7.65 (m, 1H), 7.89-7.92 (m, 1H), 7.93-7.97 (m, 2H), 7.97-8.02 (m, 2H), 8.02-8.09 (m, 1H), 8.67 (s, 1H), 12.95 (bro, 1H).

Differential Scanning calorimetry (DSC) thermograph of the benzoate salt crystals is obtained as described or similarly described herein and the DSC is depicted in FIG. 9-A. Approximately 3 mg of sample is weighed into an aluminum DSC pan and sealed hermetic lid (crimped). The sample is then loaded into a Hitachi High-Tech DSC6220ASD-2 at 30° C. The sample is heated from 30 to 250° C. at scan rate of 5° C./min and the resulting heat flow response is monitored. A 50 mL/min nitrogen purge is used to prevent thermally induced oxidation of the sample during heating and to reduce the thermal lag through the sample to increase the instrument sensitivity.

The XRPD of benzoate salt crystals is obtained as described or similarly described herein. The result is depicted in FIG. 9-B. Approximately 20 mg of sample is gently put on the XRPD glass sample holder. The sample is then loaded into a MiniFlex II and analyzed using the following experimental conditions.

Tube anode: Cu
Generator tension: 30 kV
Tube current: 15 mA
Wavelength alpha 1: 1.5406 A
Wavelength alpha 2: 1.5444 A
Start angle [2 theta]: 3
End angle [2 theta]: 40
Scan speed 6.000°/min
Scan step size: 0.02

The XRPD pattern of benzoate salt crystals is depicted in FIG. 9-B and has peaks as set forth in Table 8 below:

TABLE 8

| No | Pos. [°2Th.] | d-spacing [Å] | Height [cps] | Rel. Int. [%] |
|---|---|---|---|---|
| 1 | 6.24 | 14.1525 | 1362 | 31 |
| 2 | 7.26 | 12.1662 | 241 | 6 |
| 3 | 12.10 | 7.3084 | 1193 | 27 |
| 4 | 14.92 | 5.9328 | 438 | 10 |
| 5 | 15.84 | 5.5902 | 1154 | 26 |
| 6 | 17.20 | 5.1512 | 4461 | 100 |
| 7 | 19.62 | 4.5209 | 1966 | 45 |
| 8 | 21.80 | 4.0735 | 3536 | 80 |
| 9 | 22.68 | 3.9174 | 3428 | 77 |
| 10 | 24.44 | 3.6391 | 1050 | 24 |
| 11 | 25.42 | 3.5010 | 595 | 14 |
| 12 | 26.06 | 3.4165 | 575 | 13 |
| 13 | 27.08 | 3.2901 | 754 | 17 |
| 14 | 27.80 | 3.2065 | 909 | 21 |
| 15 | 28.64 | 3.1143 | 733 | 17 |

Example 15

Pharmaceutical Composition Comprising the Monophosphate Salt Crystals of Compound A A binder solution is prepared by dissolving hydroxypropyl cellulose (157.5 g) in purified water (2468 g). The monophosphate salt crystals of Compound A (1232 g), mannitol (2996 g), microcrystalline cellulose (367.5 g) and sodium starch glycolate (262.5 g) are charged in a fluidized bed granulator. The charged powders (5016 g) are granulated by spraying the binder solution (2626 g) in the fluid bed granulator. The granules are dried in the fluid bed granulator. The dried granules are milled using power mill with 1.5 mmΦ punching screen. The milled granules (4299 g) are blended with microcrystalline cellulose (135.0 g) and magnesium stearate (66.00 g) in a diffusion mixer. The blended granules (4200 g) are compressed into tablets by using a tablet press with a punch of 7 mmΦ at the weight of 150 mg. The tablets (3000 g) are coated with an aqueous film coating solution containing premix 1 (hypromellose 2910/polyethylene glycol 8000/titanium dioxide/ferric oxide red=9/2/1/0.2) and premix 2 (hypromellose 2910/polyethylene glycol 8000/titanium dioxide/ferric oxide yellow=9/2/1/0.2) by pan coating.

| Components | Quantity per Tablet (mg) |
|---|---|
| Compound A monophosphate salt crystal | 35.79 |
| (as the free base equivalent) | (30) |
| Mannitol | 85.01 |
| Microcrystalline Cellulose | 15.0 |
| Hydroxypropyl Cellulose | 4.5 |
| Sodium Starch Glycolate | 7.5 |
| Magnesium Stearate | 2.2 |
| Hypromellose 2910 | 4.5 |
| Polyethylene Glycol 8000 | 1.0 |

| Components | Quantity per Tablet (mg) |
|---|---|
| Titanium Dioxide | 0.5 |
| Ferric Oxide, Red | 0.05 |
| Ferric Oxide, Yellow | 0.05 |
| TOTAL | 156.1 |

The invention claimed is:

1. A crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base (Compound A) as shown by the following chemical formula:

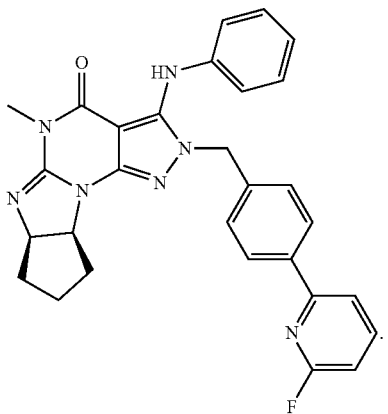 [SMILES: CN1C(=O)c2c(nn(Cc3ccc(-c4cccc(F)n4)cc3)c2Nc2ccccc2)N2C1=N[C@@H]1CCC[C@@H]12]

2. The crystal according to claim 1, wherein the crystal is in non-solvate form.

3. The crystal according to claim 1, wherein the crystal is in solvate form with alcohol.

4. The crystal according to claim 3, wherein the crystal is in solvate form with methanol, ethanol, propanol or butanol.

5. The crystal according to claim 3, wherein the crystal solvate form is mono-methanol, mono-ethanol, mono-n-propanol, mono-2-propanol or, mono-n-butanol.

6. The crystal according to claim 2, wherein the crystal is in non-hydrate or hydrate form.

7. The crystal according to claim 1, wherein said crystal exhibits an X-ray powder diffraction pattern selected from the following:
   a) an X-ray powder diffraction pattern comprising at least five peaks having d-spacing values selected from the group consisting of 14.34, 11.65, 10.83, 7.91, 7.16, 6.89, 6.59, 5.82, 5.37, 5.03, 4.87, 4.64, 4.48, 4.23, 4.06, 3.93, 3.85, 3.75, 3.59, 3.45, 3.35, 3.21, 3.14, 3.01, 2.89, 2.81, 2.74, 2.68, 2.61, 2.47, 2.42, 2.34 and 2.28 Å;
   b) an X-ray powder diffraction pattern comprising at least five peaks having d-spacing values selected from the group consisting of 14.67, 11.68, 10.96, 7.95, 7.39, 7.30, 6.80, 5.85, 5.57, 5.42, 4.86, 4.60, 4.36, 4.23, 4.14, 4.03, 3.95, 3.82, 3.71, 3.51, 3.46, 3.34, 3.22, 3.10, 3.02, 2.94, 2.91, 2.86, 2.77, 2.62, 2.55, 2.51, 2.42 and 2.33 Å;
   c) an X-ray powder diffraction pattern comprising at least five peaks having d-spacing values selected from the group consisting of 14.67, 11.53, 10.80, 7.95, 7.25, 6.93, 6.59, 5.95, 5.76, 5.41, 4.86, 4.68, 4.47, 4.33, 4.24, 4.06, 3.95, 3.82, 3.61, 3.44, 3.36, 3.25, 3.19, 3.02, 2.96, 2.87, 2.77, 2.71, 2.63, 2.58, 2.53, 2.48, 2.38, 2.35 and 2.32 Å;
   d) an X-ray powder diffraction pattern comprising at least five peaks having d-spacing values selected from the group consisting of 19.11, 12.51, 11.41, 11.01, 9.58, 8.95, 8.40, 6.60, 6.37, 6.10, 5.74, 5.33, 5.13, 4.83, 4.56, 4.39, 4.16, 3.91, 3.81, 3.58, 3.37, 3.26, 3.15, 3.03, 2.97, 2.87 and 2.84 Å;
   e) an X-ray powder diffraction pattern comprising at least five peaks having d-spacing values selected from the group consisting of 12.58, 10.75, 8.89, 7.76, 7.36, 6.95, 6.57, 6.10, 5.50, 5.16, 4.74, 4.47, 4.12, 3.96, 3.87, 3.80, 3.72, 3.63, 3.47, 3.33, 3.25, 3.14, 3.06, 2.99, 2.91, 2.86, 2.81, 2.78, 2.61, 2.56, 2.47 and 2.33 Å; and
   f) an X-ray powder diffraction pattern comprising at least five peaks having d-spacing values selected from the group consisting of 12.51, 10.80, 8.95, 7.78, 7.28, 6.93, 6.62, 6.14, 5.53, 5.13, 4.77, 4.45, 4.14, 3.96, 3.79, 3.64, 3.52, 3.40, 3.28, 3.15, 3.05, 2.65, 2.63, 2.51 and 2.47 Å.

8. The crystal according to claim 1, wherein said crystal exhibits an X-ray powder diffraction pattern selected from the following:
   a) an X-ray powder diffraction pattern comprising at least five peaks having d-spacing values selected from the group consisting of 14.34, 11.65, 10.83, 5.82, 4.87, 4.64, 4.48, 4.23, 3.93 and 3.21 Å;
   b) an X-ray powder diffraction pattern comprising at least five peaks having d-spacing values selected from the group consisting of 14.67, 11.68, 10.96, 5.85, 4.86, 4.60, 4.23, 4.03, 3.95 and 3.22 Å;
   c) an X-ray powder diffraction pattern comprising at least five peaks having d-spacing values selected from the group consisting of 14.67, 11.53, 10.80, 5.76, 4.86, 4.68, 4.47, 4.24, 4.06 and 3.95 Å;
   d) an X-ray powder diffraction pattern comprising at least five peaks having d-spacing values selected from the group consisting of 12.51, 11.41, 11.01, 9.58, 8.95, 6.60, 5.13, 4.16 and 3.81 Å;
   e) an X-ray powder diffraction pattern comprising at least five peaks having d-spacing values selected from the group consisting of 12.58, 10.75, 5.50, 4.74, 4.47, 3.96, 3.87, 3.80, 3.72 and 3.14 Å; and
   f) an X-ray powder diffraction pattern comprising at least five peaks having d-spacing values selected from the group consisting of 12.51, 10.80, 5.53, 4.77, 4.45, 4.14, 3.96, 3.79, 3.64, 3.40, 3.28 and 3.15 Å.

9. The crystal according to claim 1, wherein said crystal exhibits a Differential Scanning calorimetry (DSC) melting endotherm pattern as follows:
   a) a Differential Scanning calorimetry (DSC) pattern comprising an endothermic peak at about 107° C.-108° C.;
   b) a Differential Scanning calorimetry (DSC) pattern comprising anendothermic peak between the range of 112–118° C.;
   c) a Differential Scanning calorimetry (DSC) pattern comprising an endothermic peak at about 97° C.;
   d) a Differential Scanning calorimetry (DSC) pattern comprising an endothermic peak at about 126° C.;
   e) a Differential Scanning calorimetry (DSC) pattern comprising an endothermic peak at about 84°-85° C.;
   f) a Differential Scanning calorimetry (DSC) pattern comprising an endothermic at about 79° C., for example about 78.6° C.

10. A process for the preparation of a salt of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]-pyrazolo[4,3-e]pyrimidin-4(2H)-one (Compound A), comprising:

53

(1) dissolving a crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base (Compound A) according to claim 1 in a non-solvate or solvate form in a solvent;
(2) adding an acid optionally in a solvent, to the solution obtained in the step (1), and
(3) stirring the mixture obtained in the step (2) to result in the objective salt.

11. The process according to claim 10, wherein said salt is a salt crystal.

12. The process according to claim 10, wherein said salt crystal is selected from fumarate, phosphate, (1-hydrox-2)-naphthoate, mesylate or benzoate salt crystal.

13. The process according to claim 11, wherein the acid of step (2) is selected from fumaric acid, phosphoric acid, tartaric acid, methanesulfonic acid and benzoic acid.

14. The process according to claim 10, wherein the solvent of step (1) and/or (2) is methanol, acetonitrile, acetone or mixtures thereof.

15. A process for the preparation of a mono-phosphate salt crystal of (6aR,9aS)-5,6a,7,8,9,9a-hexahydro-5-methyl-3-(phenylamine)-2-((4-(6-fluoropyridin-2-yl)phenyl)methyl)-cyclopent[4,5]imidazo[1,2-a]-pyrazolo[4,3-e]pyrimidin-4(2H)-one (Compound A), which comprises:
(1) dissolving a crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base (Compound A) according to claim 1 in a non-solvate or solvate form, in a solvent;
(2) adding phosphoric acid in a solvent to the solution obtained in the step (1), and
(3) stirring the mixture obtained in the step (2) to result in the objective mono-phosphate salt crystal.

16. The process according to claim 15, wherein the solvent in the step (1) is selected from acetone and acetonitrile.

17. The process according to claim 15, wherein the solvent in the step (2) is selected from acetone or acetonitrile.

18. The process according to claim 15, wherein the amount of phosphoric acid to be added in the step (2) is almost (about) equimolecular quantity to the amount of crystal of the (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one free base (Compound A) in non-solvate form or in solvate form of the step (1).

19. The process according to claim 15, wherein water is additionally added in the step (2).

20. The process according to claim 15, wherein the mixture is stirred at 20 to 70° C. in the step (3).

21. The process according to claim 20, wherein the mixture is stirred at 50° C., 32° C., 38° C. or 39° C.

22. A salt crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one (Compound A) in hemi-fumarate, 0.5 ethyl acetate, 0.3 acetone solvate form; or in benzoate non-solvate form.

23. The salt crystal according to claim 22, wherein the salt crystal is in hemi-fumarate, 0.5 ethyl acetate, 0.3 acetone solvate form, and exhibit an X-ray powder diffraction pattern comprising at least five peaks having d-spacing values selected from the group consisting of: 14.67, 11.97, 10.99,

54

8.19, 7.41, 6.98, 6.46, 6.14, 5.89, 5.59, 5.20, 5.01, 4.66, 4.61, 4.30, 4.07, 3.93, 3.74, 3.59, 3.47, 3.34, 3.23, 3.06, 3.00, 2.94, 2.86, 2.80, 2.62, 2.54, 2.51 and 2.40 Å.

24. The salt crystal according to claim 22, wherein the salt crystal is in hemi-fumarate, 0.5 ethyl acetate, 0.3 acetone solvate form, and exhibit an X-ray powder diffraction pattern comprising at least five peaks having d-spacing values selected from the group consisting of: 14.67, 11.97, 7.41, 6.98, 6.46, 5.20, 5.01, 4.66, 4.30, 4.07, 3.93, 3.74 and 3.59 Å.

25. The salt crystal according to claim 22, wherein the salt crystal is in benzoate non-solvate form, and exhibits an X-ray powder diffraction pattern comprising at least five peaks having d-spacing values selected from the group consisting of: 14.15, 12.17, 7.31, 5.93, 5.59, 5.15, 4.52, 4.07, 3.92, 3.64, 3.50, 3.42, 3.29, 3.21 and 3.11 Å.

26. The salt crystal according to claim 22, wherein the salt crystal is in benzoate non-solvate form, and exhibits an X-ray powder diffraction pattern comprising peaks having d-spacing values selected from the group consisting of: 14.15, 7.31, 5.15, 4.07 and 3.92, 3 Å.

27. A process for the preparation of the crystal of (6aR,9aS)-5,6a,7,8,9,9a-hexahydro-5-methyl-3-(phenylamino)-2-((4-(6-fluoropyridin-2-yl)phenyl)methyl)-cyclopent-[4,5]imidazo[1,2-a]-pyrazolo[4,3-e]pyrimidin-4(2H)-one free base according to claim 1 (compound A) in solvate form, comprising:
(1) dissolving a salt crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]-pyrimidin-4(2H)-one (compound A) in a non-solvate or solvate form, in the mixture of an organic solvent and aqueous basic solution,
(2) separating the organic layer,
(3) adding a solvent to the organic solution obtained in the step (2), and
(4) stirring the mixture obtained in the step (3) to result in the objective crystal.

28. The process according to claim 27, wherein the crystal of (6aR,9aS)-5,6a,7,8,9,9a-hexahydro-5-methyl-3-(phenylamino)-2-((4-(6-fluoropyridin-2-yl)phenyl)methyl)-cyclopent-[4,5]imidazo[1,2-a]-pyrazolo[4,3-e]pyrimidin-4(2H)-one free base (Compound A) being prepared is in an ethanol solvate form; the salt crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]-pyrimidin-4(2H)-one (compound A) of step (1) is a hemi-fumarate salt crystal, in a non-solvate or solvate form; and the solvent of step (3) is ethanol.

29. The process according to claim 28, wherein the salt crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]-pyrimidin-4(2H)-one (compound A) hemi-fumarate in a non-solvate or solvate form of step (1) is the salt crystal of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one hemi-fumarate, 0.5 ethyl acetate, 0.3 acetone solvate.

30. The process according to claim 27, wherein the crystal of (6aR,9aS)-5,6a,7,8,9,9a-hexahydro-5-methyl-3-(phenylamine)-2-((4-(6-fluoropyridin-2-yl)phenyl)methyl)-cyclopent[4,5]imidazo[1,2-a]-pyrazolo[4,3-e]pyrimidin-4(2H)-one free base (compound A) in ethanol solvate form is a crystal of (6aR,9aS)-5,6a,7,8,9,9a-hexahydro-5-methyl-3-(phenylamino)-2-((4-(6-fluoropyridin-2-yl)phenyl)methyl)- cyclopent[4,5]imidazo[1,2-a]-pyrazolo[4,3-e]pyrimidin-4 (2H)-one free base (compound A) mono-ethanol solvate.

31. The process according to claim 15, further comprises the steps of preparing the free base crystal of Compound A.

32. A process for the preparation of a mono-phosphate salt crystal of Compound A comprising:
 (a) dissolving the salt crystal of (6aR,9aS)-5,6a,7,8,9,9a-hexahydro-5-methyl-3-(phenylamino)-2-((4-(6-fluoro-pyridin-2-yl)phenyl)methyl)-cyclopent[4,5]imidazo[1,2-a]pyrazolo[4,3-e]-pyrimidin-4(2H)-one (compound A) in hemi-fumarate in a non-solvate or solvate form, in the mixture of an organic solvent and aqueous basic solution;
 (b) separating the organic layer;
 (c) adding ethanol, to the organic solution obtained in the step (b);
 (d) stirring the mixture obtained in the step (c) to result in the objective crystal;
 (e) isolating the crystals obtained form step (d);
 (f) dissolving the crystals obtained from step (e);
 (g) adding phosphoric acid in a solvent to the solution obtained in step (b); and
 (h) stirring the mixture obtained in step (c) to result in the objective salt.

* * * * *

UNITED STATES PATENT AND TRADEMARK OFFICE
CERTIFICATE OF CORRECTION

PATENT NO. : 9,630,971 B2
APPLICATION NO. : 14/900589
DATED : April 25, 2017
INVENTOR(S) : Takashi Abe et al.

It is certified that error appears in the above-identified patent and that said Letters Patent is hereby corrected as shown below:

In the Claims

In Claim 9, Column 52, Line 62 in subpart (f), please delete the phrase ", for example about 78.6°C".

In Claim 15, Column 53, Line 24 please replace "phenylamine" with "phenylamino".

In Claim 30, Column 54, Lines 62-63 please replace "phenylamine" with "phenylamino".

Signed and Sealed this
Eighth Day of August, 2017

Joseph Matal
*Performing the Functions and Duties of the*
*Under Secretary of Commerce for Intellectual Property and*
*Director of the United States Patent and Trademark Office*